United States Patent [19]
Koenig et al.

[11] Patent Number: 6,139,546
[45] Date of Patent: Oct. 31, 2000

[54] LINEAR POWER CONTROL WITH DIGITAL PHASE LOCK

[75] Inventors: Franklin R. Koenig, Palo Alto; Bruno Strul, Portola Valley; Robin Bek, Campbell, all of Calif.

[73] Assignee: Somnus Medical Technologies, Inc., Sunnyvale, Calif.

[21] Appl. No.: 09/167,217

[22] Filed: Oct. 6, 1998

Related U.S. Application Data

[60] Provisional application No. 60/062,458, Oct. 6, 1997, provisional application No. 60/061,193, Oct. 6, 1997, provisional application No. 60/061,197, Oct. 6, 1997, provisional application No. 60/061,714, Oct. 6, 1997, provisional application No. 60/062,543, Oct. 6, 1997, and provisional application No. 60/061,213, Oct. 6, 1997.

[51] Int. Cl.$^7$ ..................................................... A61B 18/04
[52] U.S. Cl. ............................................................. 606/34
[58] Field of Search ................................. 606/32, 34, 35, 606/38, 41–50; 607/96–101, 122, 150

[56] References Cited

U.S. PATENT DOCUMENTS

| | | | |
|---|---|---|---|
| 5,233,515 | 8/1993 | Cosman | 364/413.02 |
| 5,542,916 | 8/1996 | Hirsch et al. | 604/22 |
| 5,697,909 | 12/1997 | Eggers et al. | 604/114 |
| 5,702,386 | 12/1997 | Stern et al. | 606/34 |
| 5,772,659 | 6/1998 | Becker et al. | 606/34 |
| 5,909,614 | 6/1999 | Krivoshlykov | 438/29 |
| 5,964,755 | 10/1999 | Edwards | 606/41 |

FOREIGN PATENT DOCUMENTS

| | | | |
|---|---|---|---|
| WO 97/20510 | 6/1997 | WIPO | A61B 17/39 |

*Primary Examiner*—Linda C. M. Dvorak
*Assistant Examiner*—David M. Ruddy
*Attorney, Agent, or Firm*—Wilson Sonsini Goodrich & Rosati

[57] ABSTRACT

A method and apparatus for delivery of energy by an electro-surgical instrument to a surgical site is disclosed. The apparatus delivers power to electrodes of an electro-surgical instrument during an operation performed at a surgical site. The apparatus includes a processor and a plurality of power delivery channels. The processor signals the onset of an impedance interval and a heating interval. The processor determines a target value of a control parameter to be delivered to a corresponding one of the electrodes. The plurality of power delivery channels are each coupled to the processor and to a corresponding electrode. Each of the power delivery channels responsive to signaling from the processor transitions between the impedance interval and the heating interval. Each of the power delivery channels measures, during the impedance interval, an impedance associated with a delivery of energy to the surgical site by a corresponding electrode. Each of the power delivery channels, during the heating interval, minimizes a difference between a measured value of a control parameter and the target value of the control parameter determined by the processor, to deliver the energy to the surgical site. In an alternate embodiment of the invention a method for controlling power delivery in an electro-surgical instrument is disclosed. In an alternate embodiment of the invention a method for controlling power delivery in an electro-surgical instrument is disclosed. In an alternate embodiment of the invention a method for controlling power delivery in an electro-surgical instrument is disclosed.

14 Claims, 19 Drawing Sheets

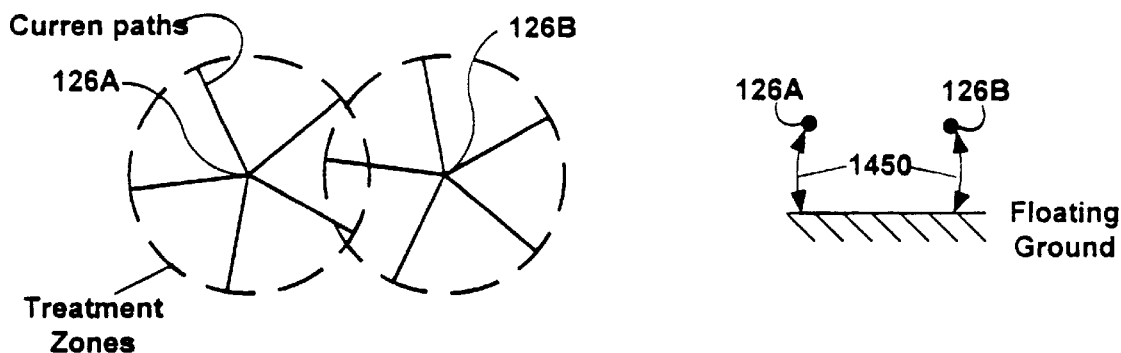
MONOPOLAR OPERATION
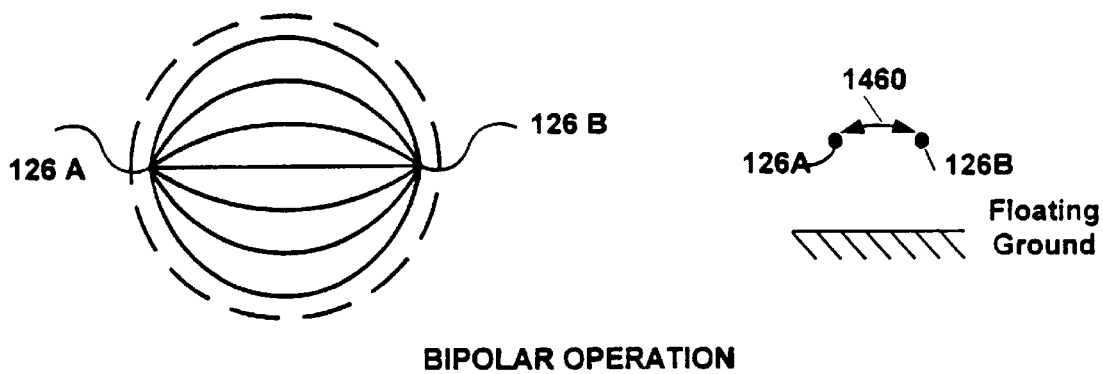
BIPOLAR OPERATION
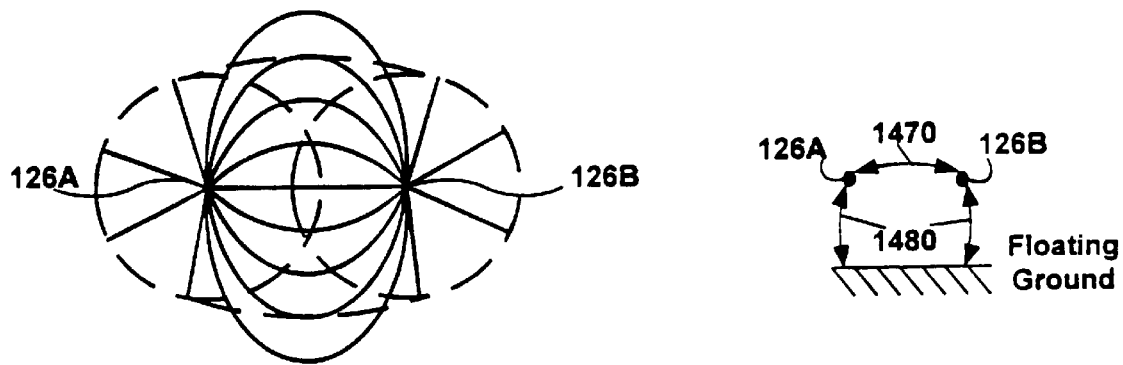
COMBINED MONOPOLAR AND BIPOLAR OPERATION
FIG. 14

LINEAR POWER CONTROL WITH DIGITAL PHASE LOCK

CROSS REFERENCE TO RELATED APPLICATION

This application claims the benefit of prior filed copending Provisional Application No. 60/062,458, filed on Oct. 6, 1997, entitled Linear Power Control With Digital Phase Lock, Provisional Application No. 60/061,193, filed on Oct. 6, 1997, entitled Linear Power Control With PSK Regulation, Provisional Application No. 60/061,197, filed on Oct. 6, 1997, entitled Memory for Regulating Device Utilization and Behavior, Provisional Application No. 60/061,714, filed on Oct. 6, 1997, entitled Dual Processor Architecture For Electro Generator, Provisional Application No. 60/062,543, filed on Oct. 6, 1997, entitled Method And Apparatus For Power Measurement In Radio Frequency Electro-Surgical Generators, and Provisional Application No. 60/061,213, filed on Oct. 6, 1997, entitled Method And Apparatus for Impedance Measurement In A Multi-Channel Electro-Surgical Generator.

The present application is related to U.S. patent application No. 09/167,412, filed Oct. 6, 1998, entitled Linear Power Control With PSK Regulation, U.S. patent application No. 09/167,222, filed Oct. 6, 1998, entitled Memory for Regulating Device Utilization and Behavior, U.S. patent application No. 09/167,508, filed Oct. 6, 1998, entitled Dual Processor Architecture For Electro Generator, U.S. patent application No. 09/167,505, filed Oct. 6, 1998, entitled Method And Apparatus For Power Measurement In Radio Frequency Electro-Surgical Generators, U.S. patent application No. 09/167,215, filed Oct. 6, 1998, entitled Method And Apparatus for Impedance Measurement In A Multi-Channel Electro-Surgical Generator, International Application No. PCT US98/21066, filed Oct. 6, 1998, entitled Linear Power Control With Digital Phase Lock, and International Application No. filed Oct. 1998, entitled Dual Processor Architecture For Electro Generator.

Each of the above-cited applications is incorporated herein by reference in its entirety.

BACKGROUND OF THE INVENTION

1. Field of the Invention

This invention relates to the field of electro-surgical medical devices. More particularly, this invention relates to devices that deliver energy in the form of radio-frequency electrical current to tissue in order to perform surgical functions.

2. Description of Related Art

Various medical procedures rely on high-frequency electrical currents to deposit energy and thus heat human and animal tissues. During such procedures, a high-frequency current is passed through the tissue between electrodes. One electrode is located at the tip of a surgical probe. Another electrode is located elsewhere, and may be a ground pad or another surgical probe tip. The tissue to be treated lies between the electrodes.

When the electrode circuit is energized, the electric potential of the electrodes at the probe tips oscillates at radio frequencies about a reference potential. If one is used, a ground pad remains at a floating reference potential. As the electric potential of the probe electrodes varies, a motive force on charged particles in the tissue is established that is proportional to the gradient of the electric potential. This electromotive force causes a net flow of electric charge, a current, to flow from one electrode, through the tissue, to any other electrode(s) at a lower potential. In the course of their flow, the charged particles collide with tissue molecules and atoms. This process acts to convert electrical energy to sensible heat in the tissue and is termed Joule heating.

Upon heating, surgical functions such as cutting, cauterizing and tissue destruction can be accomplished. For example, tissues can be cut by heating and eventually vaporizing the tissue cell fluids. The vaporization causes the cell walls to rupture and the tissue to cleave. When it is beneficial to destroy tissue, comparatively higher rates of energy deposition can cause tissue ablation.

Ablation of cellular tissues in situ is used in the treatment of many diseases and medical conditions either alone or combined with surgical removal procedures. Surgical ablation is often less traumatic than surgical removal procedures and may be the only alternative where other procedures are unsafe.

Tissue ablation devices commonly utilize electromagnetic (microwave, radio frequency (RF), lasers) or mechanical (acoustic) energy. In the category of electro-surgical devices, microwave ablation systems utilize a microwave antenna which is inserted into a natural body opening through a duct to the zone of treatment. Electromagnetic energy then radiates from the antenna through the duct wall into the target tissue. However, there is often severe trauma to the duct wall in this procedure since there is a significant microwave energy flux in the vicinity of the intended target. The energy deposition is not sufficiently localized. To reduce this trauma, many microwave ablation devices use a cooling system. However, such a cooling system complicates the device and makes it bulky. Laser ablation devices also suffer the same drawback as microwave systems. The energy flux near the target site, while insufficient to ablate the tissue, is sufficient to cause trauma.

Application of RF electric currents emanating from electrode tips offers the advantage of greater localization of the energy deposition since the electrode tip is nearly a point source. However, these devices require consideration and monitoring of the effect of the energy deposition on the tissue since the electrical dissipation and storage characteristics of the tissue carrying the current may vary with time as a result of the current-induced Joule heating. As a result, the power absorbed by the tissue and the subsequent heating response could vary over the time of treatment due to changing values of the tissue's electrical properties.

The localization of energy flux in an RF electro-surgical device may also require a number of electrodes to be included in the surgical probe to provide adequate area coverage. This may result in the electric power being delivered across several current paths. With multiple electrodes in a surgical probe, each probe electrode may or may not be at the same electric potential at each instant due to amplitude, frequency, or phase variations in their RF oscillations. If each probe electrode is at the same potential, then a current will flow between the probe electrode and the ground pad. This mode of operation is termed monopolar. If, however, each probe electrode is not at an identical potential, current will flow between the probe electrodes. This mode of operation is termed multipolar. If there are potential differences between the probe electrodes and there is a ground pad, then there are currents between the probe electrodes as well as currents between the probe electrodes and the grounding pad. This mode of operation is a combination of monopolar and multipolar modes. It is noteworthy that in the case of multipolar operation, the probe electrodes are electrically coupled by the currents flowing between them. The extent of the coupling is primarily determined by the difference in electric potential between the probe electrodes and the electrical properties of the tissue between the electrodes. This coupling can confuse monitoring of applied power and tissue response.

This invention is an improved method and apparatus for power delivery and control in an electro-surgical device. It is improved over the prior art in several areas.

First, this invention has an improved RF waveform synthesis system. Prior art methods for RF waveform synthesis in electro-surgical devices often produce square waveforms repeating at radio frequencies. This approach, however, has the drawback that substantial filtering must be applied to remove the high-frequency Fourier components of the RF squarewave. This is necessary to comply with FCC regulations on emitters. The required filtering, typically achieved with a resonant inductor-capacitor (LC) circuit, degrades the control of the relative voltages at the electrode tips by requiring a sharp bandpass filter (a filter with high quality factor, Q). With a high Q filter, small differential variations in the tuning of the electrode channels (due, for example, to aging of the capacitors and inductors) lead to differential voltages at the electrode tips. As described, this can confuse monitoring of the power applied to the surgical site by inducing electrode coupling, termed cross-talk. The novel waveform synthesis system of this invention enables the use of low Q filters thus improving tuning and reducing electrode cross-talk.

Second, this invention has an improved power measurement system. Prior art approaches for determining the power on an electrode circuit utilize high speed analog multipliers to multiply measured current and voltage signals. A drawback to these approaches is that high speed, high-precision analog multipliers and associated root mean square (RMS) converters are expensive. The novel power measurement system of this invention utilizes less expensive hardware components arranged such that they are insensitive to the reactive component of power, thus enabling improved determination of the medically relevant quantities.

Third, this invention has an improved method for electric impedance determination. With an electro-surgical device, the tissue heating response depends largely on the electrical impedance since impedance is a representation of energy dissipation and storage properties. As described, the impedance of the tissue lying between the electrodes is an important parameter both in the case of a single electrode, as well as in the case of devices with multiple electrodes. In fact, tissue electrical impedance is often displayed to the medical practitioner during a procedure since large changes in tissue impedance are indicative of tissue drying, ablation, etc.. Prior art methods for determining the electrical impedance of the tissue in the context of a device for electro-surgery are of questionable accuracy since the measurements are made at a comparatively low electric current. In the prior art methods, the electric current utilized to determine the impedance is insufficient to damage the tissue. However, the resulting measurements are prone to error since the electrical signals are not strong relative to the noise in the measurement circuit. Prior art methods also do not adequately eliminate electrode cross-talk, in the case of a multiple electrode probe. The novel impedance determination method of this invention enables measurements with a significantly greater signal-to-noise ratio and an insignificant degree of electrode cross-talk, thus improving the monitoring and control of the surgical procedure.

Fourth, this invention discloses a novel technique to control power delivery and monopolar/multipolar operation over electrodes connected to differential, time-varying tissue loads. Power control is critical in an RF electro-surgical device since it is directly related to the intended medical effects. The power absorbed by the tissue can vary over the time of treatment due to changing values of the tissue's electrical properties. This variation is due to a relation well-known to those skilled in the art in which the instantaneous power delivered to the tissue load is proportional to the square of the instantaneous electrode voltage and inversely proportional to the instantaneous tissue electrical impedance. Thus, to achieve equal power delivery, two surgical probe electrodes may have to be at different electric potentials (voltages) because of Joule heating effects on the tissue electrical impedance, or because of impedance gradients in the tissue. However, when the surgical probe electrodes are at different electric potentials, a cross-talk current will flow between the electrodes, confusing accurate power determination in most RF electro-surgical devices. This invention enables improved control of the electrode currents and monopolar/multipolar operation. The improvement can be used to better control power delivery and significantly disable electrode cross-talk during the tissue heating or to enable controllable inter-electrode current flow.

SUMMARY OF THE INVENTION

A method and apparatus for delivery of energy by an electro-surgical instrument to a surgical site is disclosed. The electro-surgical instrument may be equipped with a plurality of electrodes to deliver RF energy to the surgical site. In an embodiment of the invention accurate impedance measurement and power delivery is accomplished by dedicating discrete time intervals to each of these functions. In another embodiment of the invention a waveform generator is disclosed which utilizes a digitally generated oscillating waveform by which energy is transferred to the site. In another embodiment of the invention switching circuitry is disclosed which allows adjustment of the power level without alterations to the frequency, amplitude or phase of the oscillating waveform. In another embodiment of the invention an inexpensive circuit for measuring actual power delivered by each electrode to the surgical site is disclosed.

In an embodiment of the invention an apparatus for delivering power to electrodes of an electro-surgical instrument during an operation performed at a surgical site is disclosed. The apparatus includes a processor and a plurality of power delivery channels. The processor signals the onset of an impedance interval and a heating interval. The processor determines a target value of a control parameter to be delivered to a corresponding one of the electrodes. The plurality of power delivery channels are each coupled to the processor and to a corresponding electrode. Each of the power delivery channels responsive to signaling from the processor transitions between the impedance interval and the heating interval. Each of the power delivery channels measures, during the impedance interval, an impedance associated with a delivery of energy to the surgical site by a corresponding electrode. Each of the power delivery channels, during the heating interval, minimizes a difference between a measured value of a control parameter and the target value of the control parameter determined by the processor, to deliver the energy to the surgical site.

In an alternate embodiment of the invention a method for controlling power delivery in an electro-surgical instrument is disclosed. The electro-surgical instrument includes a plurality of channels for delivery of an energy to a surgical site. The method for controlling power comprising the acts of:

measuring in a first time interval, the impedance of each of said channels, and each channel sequentially isolated from others of the channels to determine impedance;

generating in a second time interval for each of the channels a signal proportional to an actual power in each of the channels, and the signal proportional to the actual power derived from a product of low frequency signals proportional to current and voltage of each of the channels and the low frequency signals derived from high frequency signals corresponding to a current and a voltage on each of the channels; and adjusting in the second time interval, power levels of the channels to minimize a difference between a measured value of a control parameter and a target value of the control parameter, to deliver the energy to the surgical site.

In an alternate embodiment of the invention a method for controlling power delivery in an electro-surgical instrument is disclosed. The electro-surgical instrument includes a plurality of channels for delivery of an energy to a surgical site. The method for controlling power comprises the acts of:

measuring in a first time interval, the impedance of each of plurality of channels by sequentially isolating each of the plurality of channels from others of the plurality of channels; and computing in a second time interval differences between a target power and an actual power delivered to the plurality of channels to establish an amount by which to increase and to decrease the power in the plurality of channels; and modulating in the second time interval a driver signal for each of the plurality of channels to increase and to decrease an integer number of whole wavelengths of the driver signal to produce power levels on each of the plurality of channels, responsive to the computing act.

In an alternate embodiment of the invention a method for controlling power delivery in an electro-surgical instrument is disclosed. The electro-surgical instrument includes a plurality of channels for delivery of an energy to a surgical site. The method for controlling power comprises the acts of:

generating for a first of the plurality of channels a signal proportional to an actual power, and the signal proportional to the actual power derived from a product of low frequency signals proportional to current and voltage of the first of the plurality of channels and the low frequency signals derived from high frequency oscillating signals corresponding to a current and a voltage of a first oscillating signal of the first of the plurality of channels;

computing differences between a target power and an actual power delivered to the first of the plurality of channels to establish an amount by which to increase and to decrease the power in the first oscillating signal; and modulating a driver signal generated by the driver to increase and to decrease an integer number of whole wavelengths of the driver signal to produce the first oscillating signal, responsive to said computing act.

BRIEF DESCRIPTION OF THE FIGURES

FIG. 14 illustrates the monopolar, multipolar and combined monopolar/multipolar modes of operation.

DETAILED DESCRIPTION

A method and apparatus for delivery of energy by an electro-surgical instrument to a surgical site is disclosed. The electro-surgical instrument may be equipped with a plurality of electrodes to deliver RF energy to the surgical site. In an embodiment of the invention accurate impedance measurement and power delivery is accomplished by dedicating discrete time intervals to each of these functions. In another embodiment of the invention a waveform generator is disclosed which utilizes a digitally generated oscillating waveform by which energy is transferred to the site. In another embodiment of the invention switching circuitry is disclosed which allows adjustment of the power level without alterations to the frequency, amplitude or phase of the oscillating waveform. In another embodiment of the invention an inexpensive circuit for measuring actual power delivered by each electrode to the surgical site is disclosed.

Figure 1A:
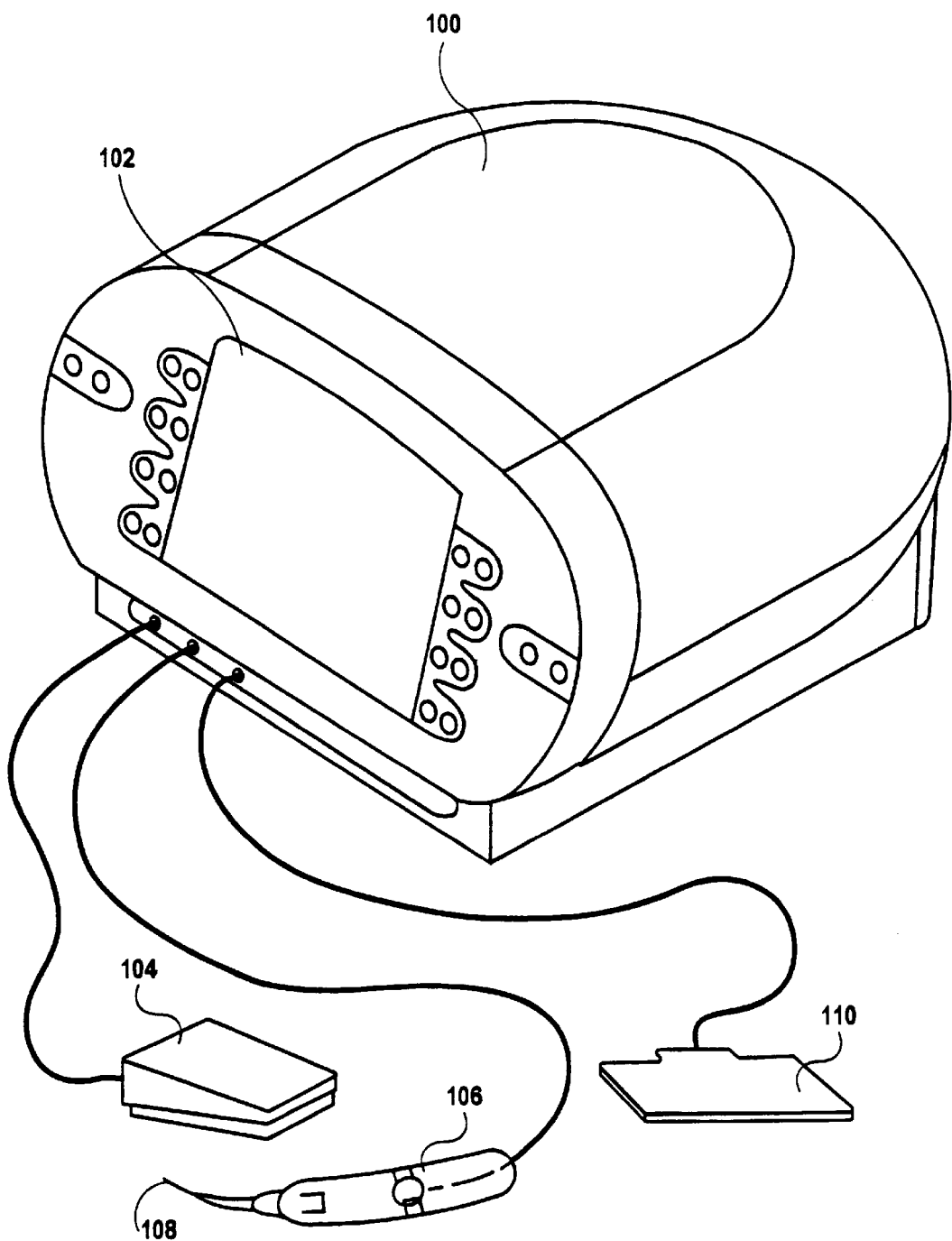
FIG. 1A shows an illustrative embodiment of a RF treatment system.

FIG. 1A shows the apparatus for a typical embodiment of the RF electro-surgical device. The system comprises an RF power supply 100 with a user input and display panel 102, a foot switch 104, a surgical handset 106 with a surgical probe 108 and an electrical grounding pad 110.

The RF power supply 100 converts the low frequency electrical energy supplied by a wall connection (not shown) into the high frequency or RF energy necessary for surgery. The user input and display panel 102 displays relevant parameters and provides buttons and switches for user input to the control systems. The foot switch 104 connected to the power supply provides means for switching the unit on and off. The surgical handset 106 is also connected to the power supply and is the means for delivering the RF energy to the surgical probe 108. The probe has one or more electrodes. The electrical grounding pad 110 is also connected to the power supply. (note to inventor: Other embodiments have no grounding pad.

Figure 1B:
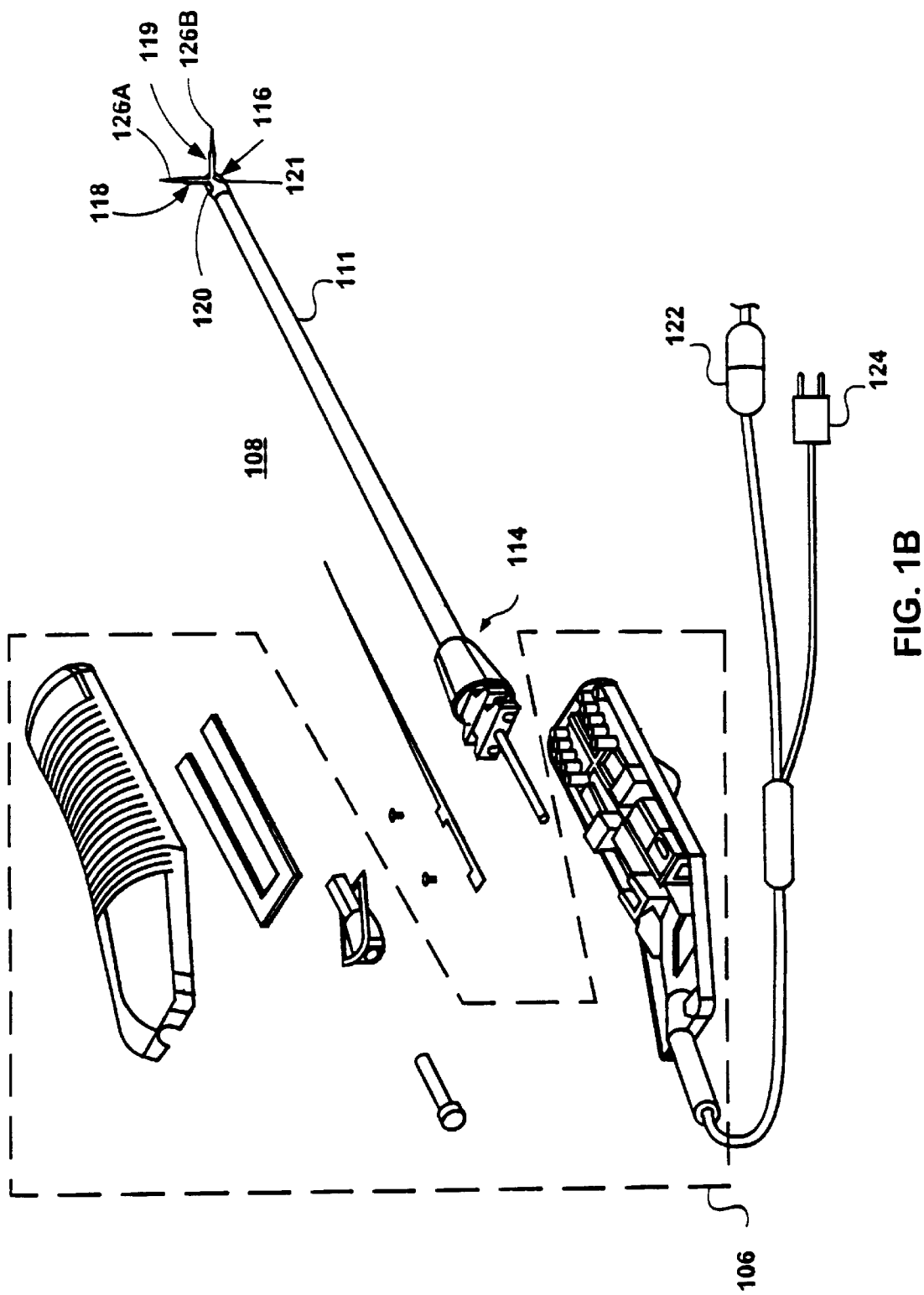
FIG. 1B shows an exploded perspective view of the surgical handset.

FIG. 1B is an exploded perspective view of the surgical handset 106 and surgical probe 108. As shown, the surgical probe 108 includes a flexible catheter 111 which is attached to a surgical handset 106 by a connector 114. The flexible catheter 111 includes a distal tip 116 having two stylets 118, 119, which extend outward from stylet ports 120, 121. Each stylet has a probe electrode 126 A–B. The surgical handset 106 includes an RF power connector 122 and a thermocouple connector 124.

The flexible catheter 111 preferably has a stiffness gradient for easier insertion through a natural body opening into a body duct. For example, the flexible catheter 111 can be relatively stiff near the surgical handset 106 and more flexible near the distal tip 116. The flexible catheter 111 can be constructed of an inner slotted stainless steel tube with an outer flexible sleeve, such as the catheter described in detail in copending application Ser. No. 08/126,431 filed Sep. 24, 1993, now U.S. Pat. No. 5,322,064, the entire contents of which are incorporated herein by reference. The catheter may also be constructed of a coiled or braided wire having a bonded outer sleeve.

Figure 1C:
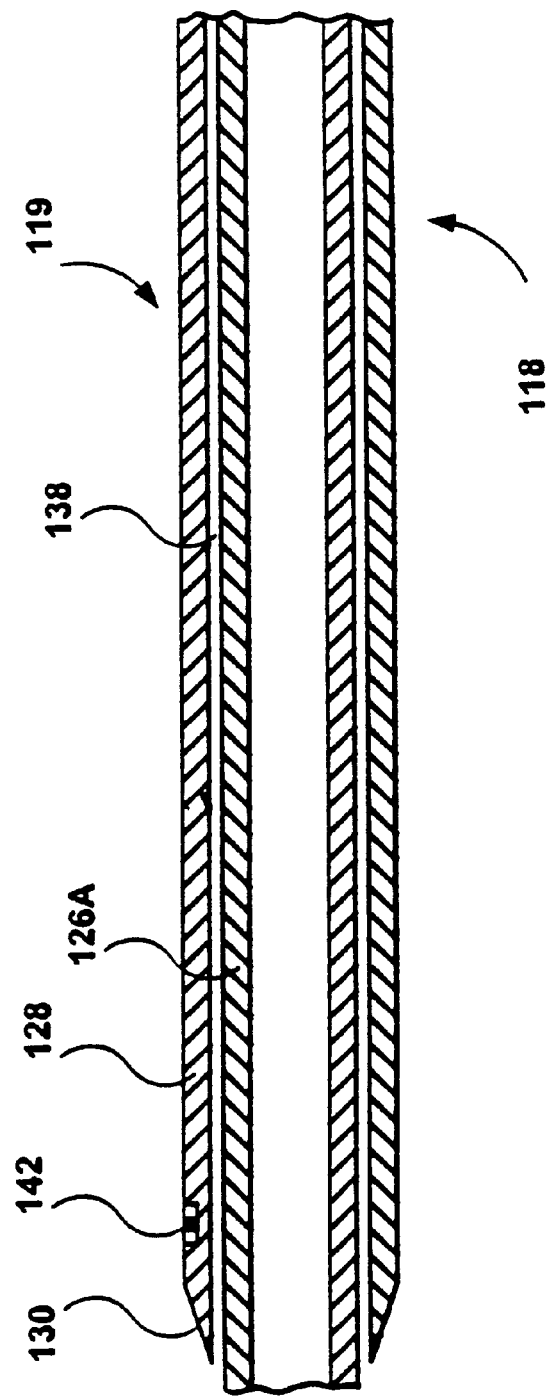
FIG. 1C shows a cross-sectional view of a stylet of the RF heating device.

FIG. 1C is a cross-sectional view of a stylet such as 118 or 119. Each stylet includes a probe electrode 126 A–B enclosed within a retractable insulating sleeve 128. The stylets are described in detail in the copending application Ser. No. 08/012,370 filed Feb. 2, 1993, now U.S. Pat. No. 5,370,675. As shown in FIG. 1C, the insulating sleeve 128 has a tapered tip 130. The probe electrode 126 is disposed in the center portion 138 of the insulating sleeve 128 such that it can slide within the sleeve. A thermocouple 142 is mounted near the tapered tip 130 of the insulating sleeve 128 for measuring the temperature of a target tissue as it is heated.

Figure 2:
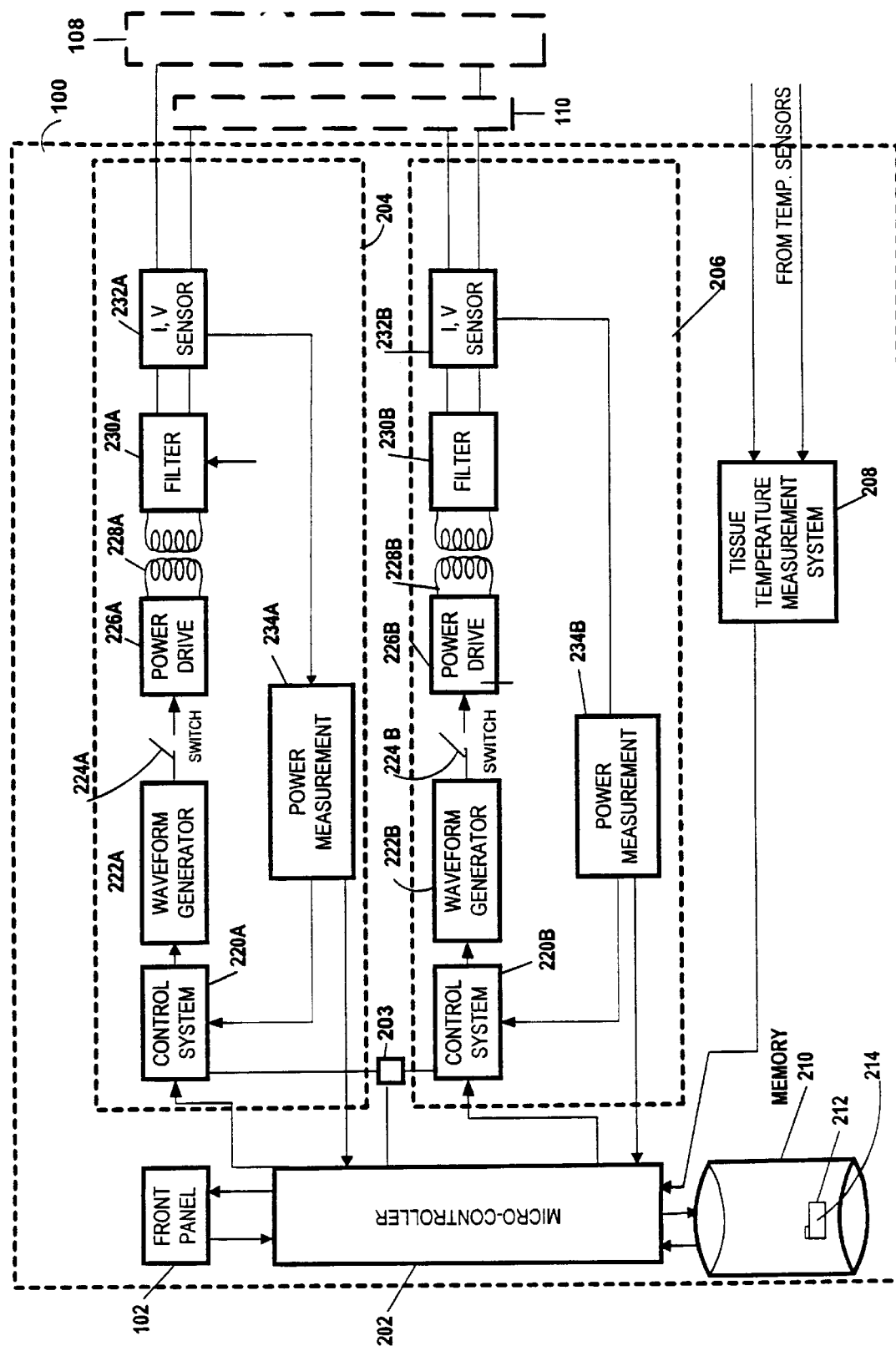
FIG. 2 shows a block diagram showing elements of the system architecture.

FIG. 2 shows a block diagram showing elements of the system hardware architecture of an exemplary embodiment. FIG. 2 shows a block diagram of the RF power supply 100, surgical probe 108 and grounding pad 110. Within the power supply, the user input and display panel 102, micro-controller 202, first and second electrode channels 204 and 206, tissue temperature measurement system 208, memory unit 210, memory files 212, control parameter schedule 214, and RF oscillator 203 are indicated. Electrode channels 204 and 206 are identical, each comprising a control system 220 A–B, waveform generator 222 A–B, an isolation switches 224 A–B, a power drive 226 A–B, a transformer 228 A–B, a filter 230 A–B, current and voltage sensors 232 A–B, and power measurement system 234 A–B.

In FIG. 2, the user input and display panel 102 is connected to the micro-controller 202 which is connected to the memory unit 210 including memory files 212, including a control parameter schedule 214. The control parameter schedule, a.k.a. profile contains data correlating target control parameters, e.g. temperature and power as a function of time. Exemplary control parameters are power and tissue temperature at the surgical site. Other control parameters are apparent to persons skilled in the art. The micro-controller is connected with the identical electrode channels 204 and 206 and also to the tissue temperature measurement system 208 and the RF oscillator 203. Within each electrode channel, the control systems 220 A–B are connected to the micro-controller as well as to the RF oscillator and the tissue temperature measurement system. The control system also connects to the waveform generators 222 A–B. The waveform generators are connected to the power drive 226 A–B through the isolation switches 224 A–B. It is obvious tho persons skilled in the art that the isolation switches 224 A–B may be located elsewhere than shown in FIG. 2. It is equally obvious that the switching function may be performed by other hardware elements in FIG. 2. The RF signals from the transformers 228 A–B feed into filters 230 A–B. The current and voltage sensors 232 A–B connect to the filter, grounding pad 110, surgical probe 108 and the power measurement systems 234 A–B.

The micro-controller 202 implements control programs and logic contained in memory files 212, providing the principal intelligence of the control system including the selection of values for time scales and power levels. In other embodiments, the control functions are divided between the micro controller and the control system 220 A–B. In an embodiment, the microcontroller provides target values of a control parameter to the control system. The control system adjusts drive levels to match the actual power as measured by the power measurement circuit with the target values of the control parameter from the microcontroller. In another embodiment of the invention the micontroller cycles each channel between an impedance measurement interval and a heating interval. During the impedance measurement interval power is applied to each channel individually and at a level higher than used during the heating interval.

To act as a means for control, the micro-controller is in two way communication with the user through user input and display panel 102 as well as receives input from the RE oscillator 203, power measurement system 234 A–B, and tissue temperature measurement system 208 A–B. The micro-controller is also coupled to memory unit 210 from which it can obtain the control parameter schedule 214. Control variables are passed to control systems 220 A–B to achieve the desired amplitude, frequency, and phase of the electrode potentials.

The RF oscillator 203 and waveform generator 222 A–B generate RE oscillations, termed a driver signal 223 A–B. The driver signal, or a modulated driver signal 225 A–B incorporating on-off switching with the driver signal, drives the output of the power drive 226 A–B. The modulation of the driver signal is determined by the micro-controller. It is obvious to persons skilled in the art that isolation switches 224 A–B may be located in a variety of positions other than shown in the embodiment of FIG. 2. Power is coupled through transformer 228 A–B by the principle of induction, isolating the patient from direct current (DC). Further frequency filtering is accomplished by filter 230 A–B. Collectively components 220 A–B through 226 A–B constitute drive units for which there are numerous alternate embodiments known to those skilled in the art. Numerous substitutions are possible for the above described components without departing from the teachings of this invention.

Current and voltage sensors 232 A–B provide required signals for the power measurement systems 234 A–B to determine the actual power, a.k.a. true power or non-reactive power, transferred to the tissue by the current passing between the surgical probe 108 to grounding pad 110. Once the actual power is determined in the power measurement systems 234 A–B the results are passed to micro-controller 202. The micro-controller compares the actual power to the desired power level and obtains the difference between the two. If the actual power is less than the desired power, a.k.a. target power, then either or both the waveform generator(s) 222 A–B and/or the power drives 226 A–B is controlled to increase power. Conversely if the actual power is greater than the desired power then either or both the waveform generator(s) and/or the power drives is controlled to decrease power.

In an embodiment of the invention the target power is fixed over the course of the operation. In another embodiment of the invention the control parameters for the operation vary as a function of time. That schedule of power or temperature as a function of time is recorded in memory unit 210 and specifically the control parameter schedule 214. During the course of the surgical operation the micro-controller will update target parameters, e.g. power or temperature, using the power/temperature schedule and an internal timer which is initialized at the start of surgery. Thus the micro controller periodically updates power/temperature targets on the basis of the data stored in the power/temperature schedule. These target levels are compared with actual power levels and the micro controller adjusts the drive level of either or both channels 204–206 to reduce the difference between the actual power and the target power. In another embodiment of the invention in which the power/temperature schedule contains only target temperatures the micro controller uses the actual power measurements to adjust drive levels so as to maintain target temperatures at the surgical site.

Micro-controller 202 can differentially control the voltage waveforms of each electrode in the surgical probe 108. In alternate embodiments, analog hardware in control system 220 A–B performs this function. By altering the amplitude, frequency, or phase, as well as by introducing null intervals to the voltage applied to each electrode tip, the electric power transferred to the tissue in the face of changing tissue electrical impedance can be controlled over the time of the surgical procedure.

Figure 3:
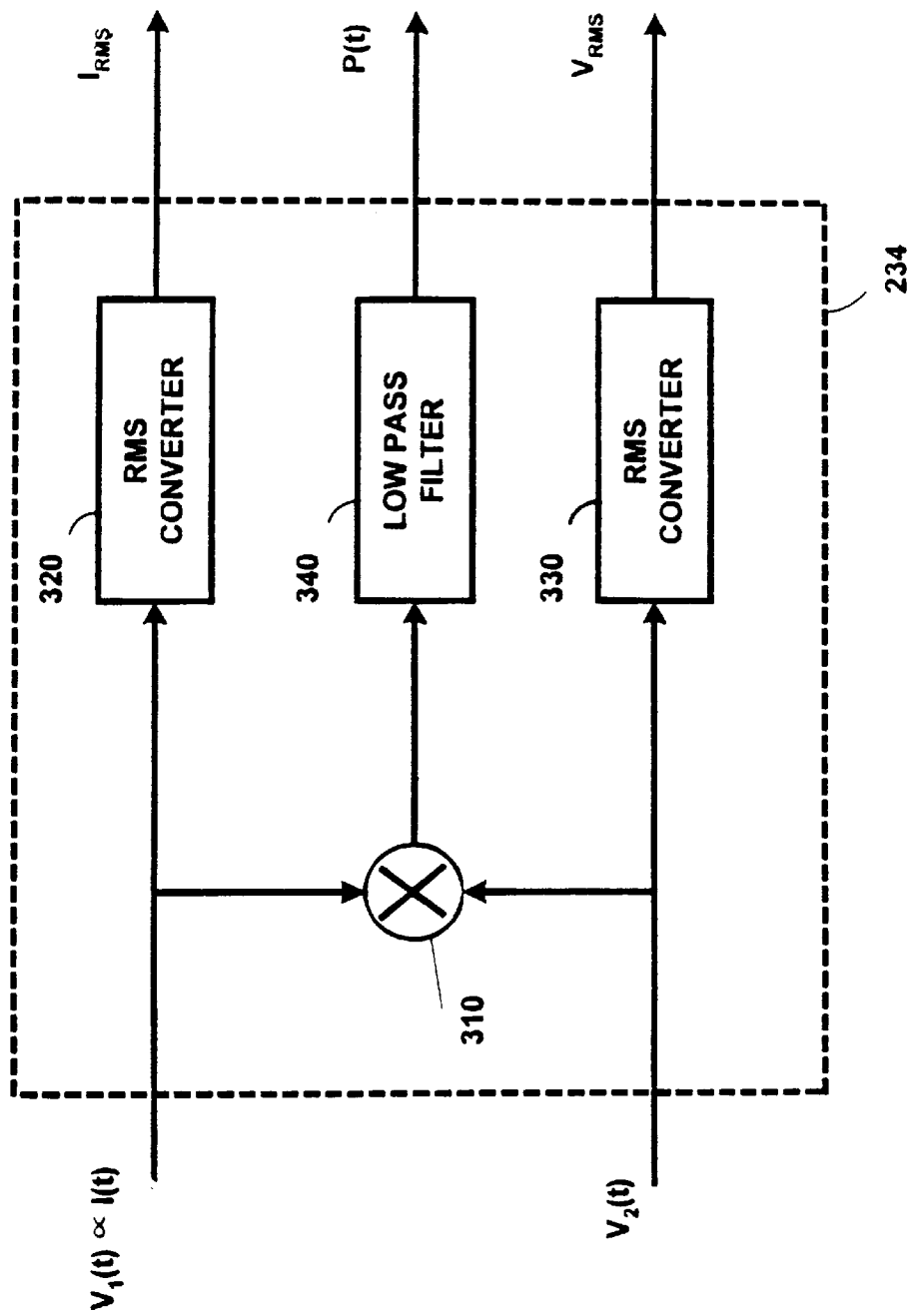
FIG. 3 shows a prior art power measurement system.

FIG. 3 is a prior art electric power measurement system 234. This system includes a a high speed analog multiplier 310, and RMS converters 320 and 330, and a low pass filter 340.

In FIG. 3, high speed analog multiplier 310 multiplies input voltages. One voltage represents the electric potential difference across the electrode channel and another voltage is proportional to the current flowing through the patient on that channel. The product of these voltages is proportional to and represents the instantaneous power being delivered to the patient. Low pass filter 340 filters the instantaneous power signal to provide a signal representative of the average power delivered to the patient on that channel. This is the quantity of interest to the medical practitioner. RMS converters 320 and 330 transform their respective RF inputs into slowly varying signals that represent the root mean square values of the current and voltage being delivered to the patient. The chief disadvantage of the prior art approach in FIG. 3 is that it requires the use expensive components such as a high speed, high precision analog multiplier and high speed RMS converters.

Figure 4:
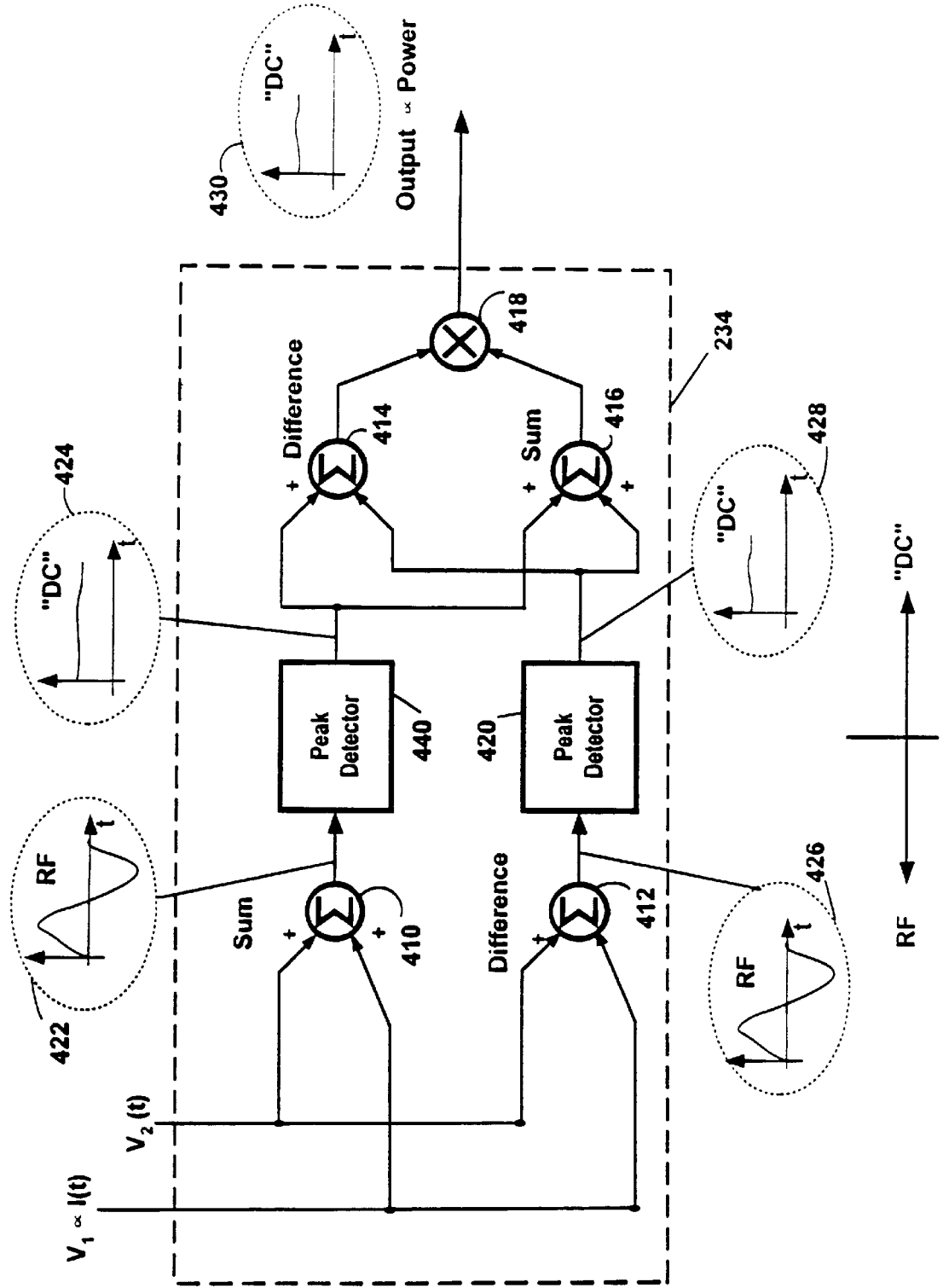
FIG. 4 shows the preferred embodiment of the power measurement system of the current invention.

FIG. 4 shows the power measurement system 234 of the preferred embodiment of this invention. The chief advantage of this embodiment is that it does not require the use of a high speed analog multiplier. It can use a much less expensive low speed precision analog multiplier. It also does not require the use of RMS converters. However, to retain accuracy, it requires the input signals to be sinusoidal.

The embodiment illustrated in FIG. 4 consists of summing amplifier 410 and differencing amplifier 412, i.e. the first summer and differencer; peak detectors 420 and 440; summing amplifier 416 and differencing amplifiers 414, i.e. the second summer and differencer; and low speed analog multiplier 418.

The inputs to the system in FIG. 4 are voltage and current signals from sensors 232 A–B (See FIG. 2) that represent the instantaneous voltage and instantaneous current in a channel of the loaded circuit. In the this embodiment of the invention the input current and voltage signals are high frequency sinusoidal waveforms, with negligible DC offset.

Summing amplifier 410 produces a voltage 422 that is the sum of the current and voltage signals and oscillates at radio frequencies. Similarly, differencing amplifier 412 produces a voltage 426 which represents the difference of the current and voltage signals and oscillates at radio frequencies. The output of summing amplifier 410 feeds into peak detector 440 which transforms the input into a slowly varying voltage 424 that is representative of the peak amplitudes of the sinusoid from summing amplifier 410. Similarly, peak detector 420 produces a slowly varying voltage 428 that is representative of the peak amplitude of the sinusoid from differencing amplifier 412. It can be readily appreciated that the proportionality of the time integrals of the signals from the peak detectors and those of their inputs is preserved if the inputs have an invariant waveform, e.g. sinusoidal.

Summing amplifier 416 and differencing amplifier 414 are low speed devices. They accept as inputs the "DC", e.g. steady state, outputs of peak detectors 440 and 420. Differencer 414 produces an output signal proportional to the difference in the outputs of peak detectors 440 and 420. Summer 416 produces an output signal that is proportional to the sum of the outputs of the peak detectors. The outputs of summing amplifier 416 and differencing amplifier 414 are multiplied by low speed analog multiplier 418 to produce a slowly varying voltage 430 that is proportional to the actual power applied on the channel to the load. This power output signal can be converted to one which is equivalent, as opposed to proportional, to the actual power by applying a coefficient to the multiplication process performed by low speed analog multiplier 418. Note that the power output signal is proportional to the non-reactive component of power. This non-reactive component represents the electric power absorbed by the tissue in a medical procedure.

Electric power determination enables feedback control of a power delivery system. For consistency with the method of power determination, the method of RE waveform synthesis of this invention delivers sinusoidally varying power to each electrode channel.

Figure 5:
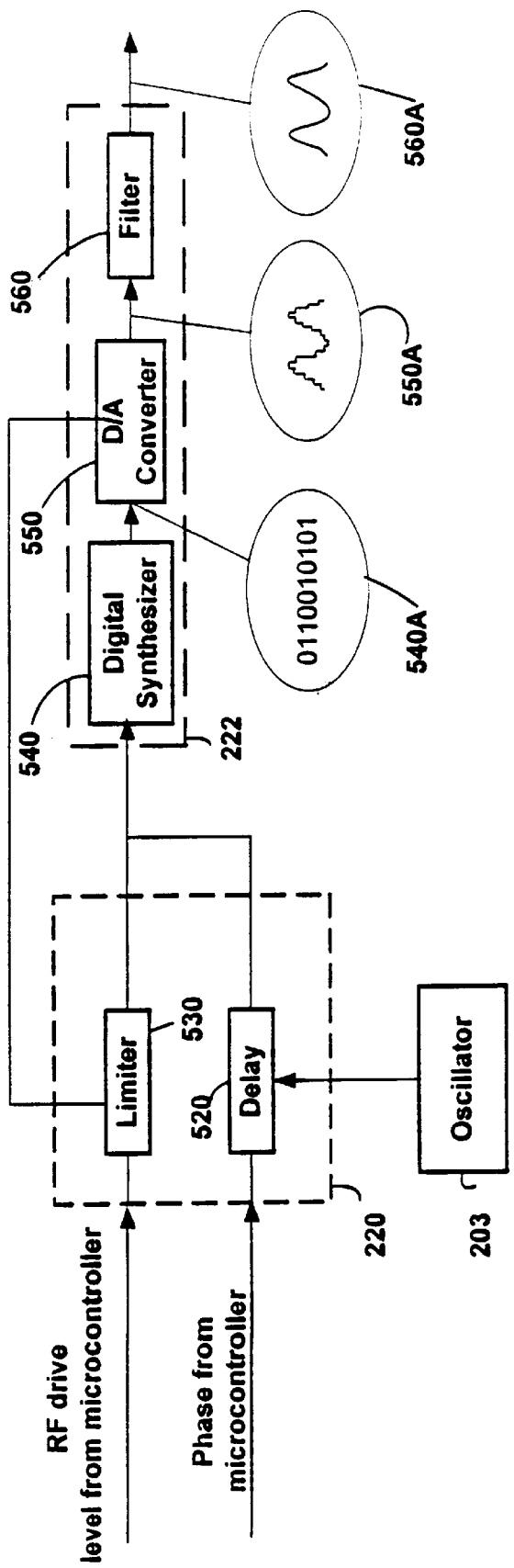
FIG. 5 shows a schematic of the RF waveform synthesis system for a single electrode channel.

FIG. 5 is a schematic of the RF waveform synthesis system for a single electrode channel showing the control system 220 and waveform generator 222 and RF oscillator 203 (see FIG. 2). In FIG. 5, the control system is comprised of adjustable delay generator 520 and RF drive level limiter 530. The waveform generator 222 comprises a digital synthesizer 540, digital-to-analog converter 550 and filter 560.

The control system 220 shown in FIG. 5 receives input from the RF oscillator 203 and micro-controller 202 (see FIG. 2). The micro-controller provides the RF drive level and a phase-controlling signal. Phase input from the micro-controller and input from the RF oscillator is processed by adjustable delay generator 520. Output from the delay generator is passed to the waveform generator 222 as is the RF drive level, after passing limiter 530.

The RF oscillator 203 provides a time base for the control system. The adjustable delay generator 520, along with the input phase data from the micro-controller allow a controllable phase difference in the power applied over different electrode channels in a multi-channel device. The limiter 530 serves to prevent a predetermined RF drive level from being exceeded. The phase information from the control system is passed to the digital synthesizer 540 which, acting with a stored look-up table, sends a time series of binary digits, e.g. 540A, to the digital-to-analog (D/A) converter 550. The output of the D/A converter is an analog waveform, e.g. 550A. Filter 560 creates a clean sinusoid, e.g. 560A, from this signal by filtering out the higher frequency components of the waveform, as shown in FIG. 5.

Figure 6:
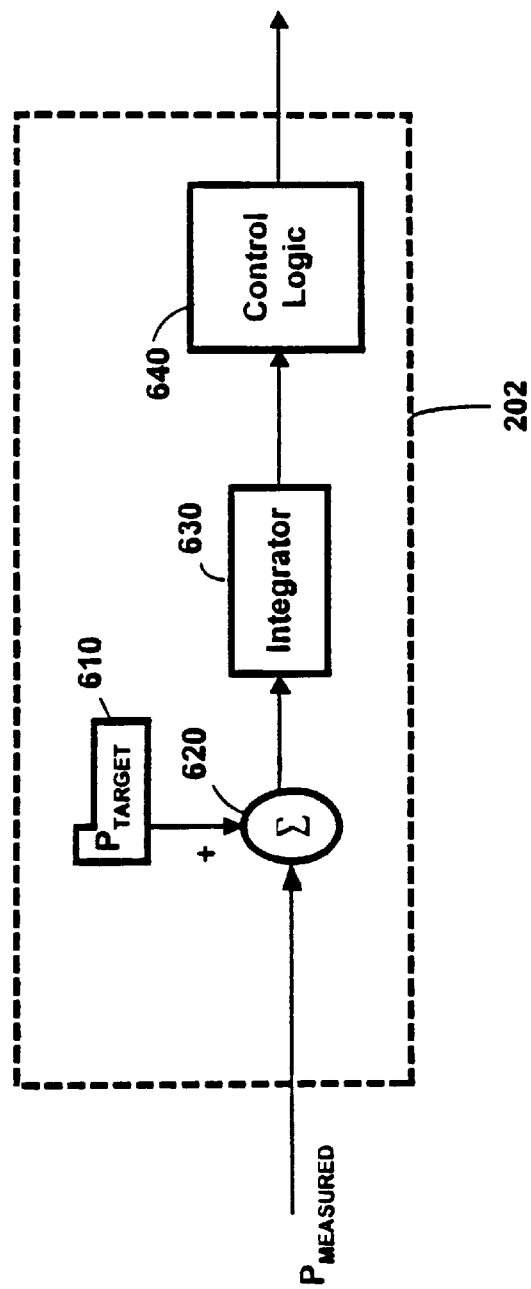
FIG. 6 shows the generation of the control system feedback.

FIG. 6 shows the process for generating the control system feedback in the micro-controller 202. In FIG. 6, the power determined by direct measurement of the electrode voltage and current in the power measurement system 234 (see FIG. 2, FIG. 4) is compared to the target power schedule 610 in differencing element 620.

The resulting difference is integrated over an adjustable time by integrating element 630. Control logic 640 is implemented to drive the difference between the target power and the power determined by measurement to zero by adjusting the micro-controller output that is sent to the control system 220.

Figure 7:
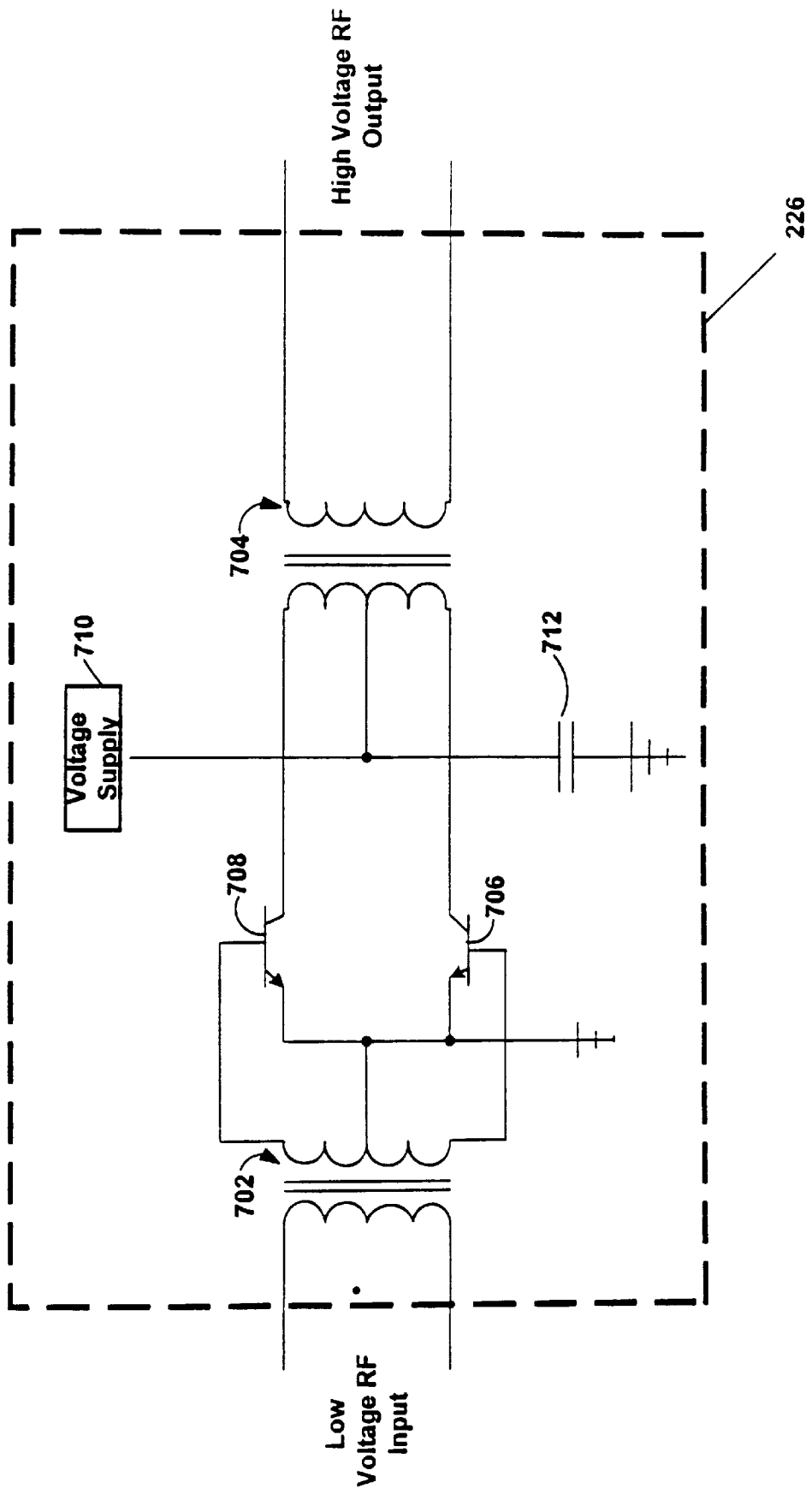
FIG. 7 shows a schematic illustrating the electrical hardware elements of a power drive element

FIG. 7 shows a schematic illustrating the electrical hardware elements of a power drive 226. The power drive contains two transformers 702 and 704, two transistors 706 and 708, positive voltage supply 710 and an isolating capacitor 712.

In FIG. 7, transformer 702 is connected to the RF oscillator on one side and the transistors 706 and 708 on its other side. The center tap of the transformer is also connected to the transistors 706 and 708. The winding of the second transformer 704 are connected to the positive voltage supply 710 and isolation capacitor 712 on one side and on the other side they form the output of the device.

The transformer 702 serves to isolate the unit from the RIF waveform generator 222 (see FIG. 2) that provides its input. Through the principal of electrical induction, radio frequency oscillations are induced in the RF power supply from the RF waveform generator. The positive voltage supply 710 in conjunction with the second transformer 704 act to modulate the amplitude of the RF voltage in the circuit. Through the principal of electrical induction the RE signals are transferred to the output across the transformer 704.

Figure 8:
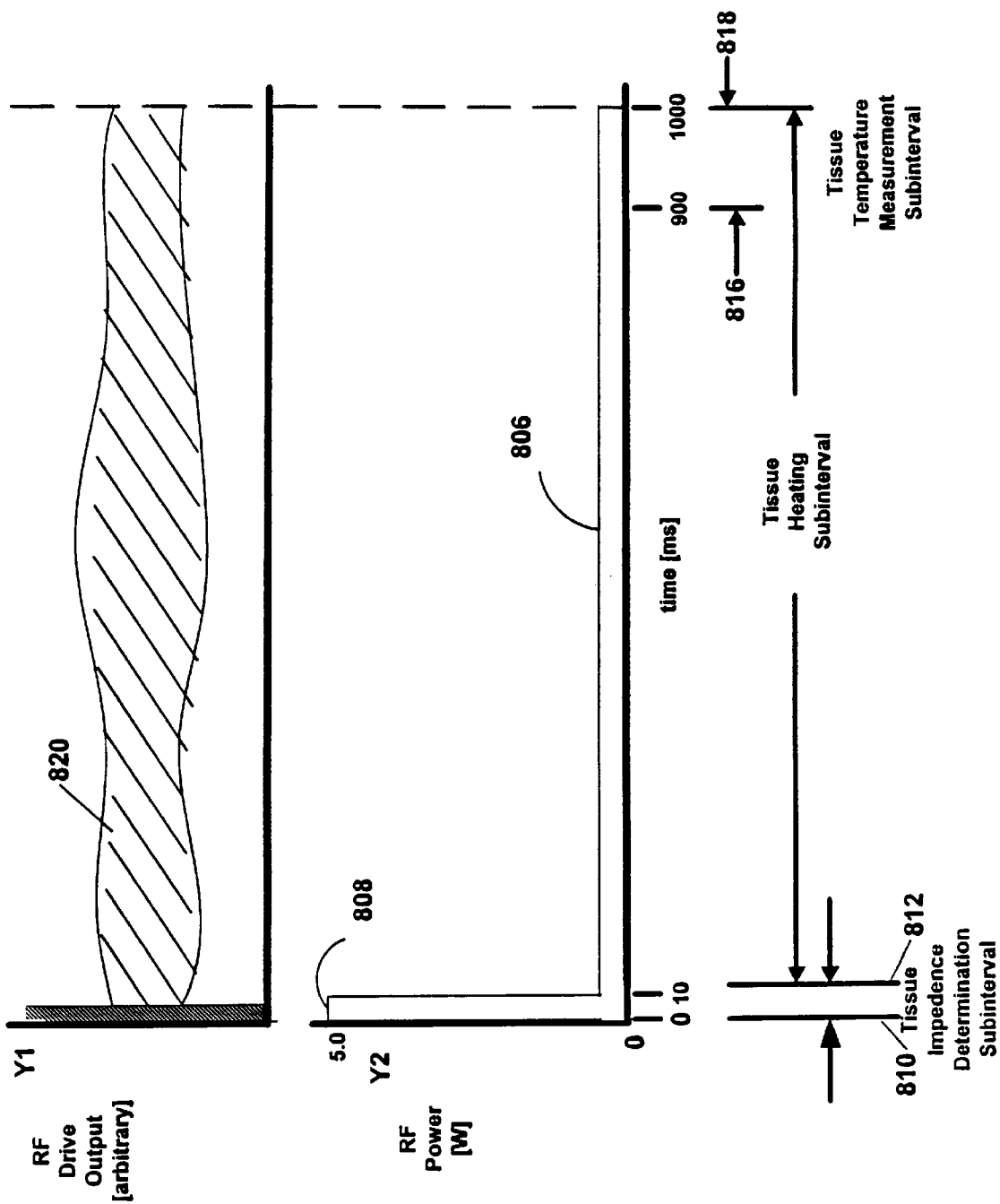
FIG. 8A shows a graph of power versus time for a single electrode probe illustrating the time sub-intervals for impedance determination, tissue heating and tissue temperature measurement.
FIG. 8B shows a graph of RF power supply drive parameter versus time for a single electrode probe illustrating the time sub-intervals for impedance determination, tissue heating and tissue temperature measurement.

FIG. 8A and FIG. 8B show graphs of power versus time and RF power supply drive parameter versus time for a single electrode probe. FIGS. 8A–B illustrate the time interval multiplexing of an overall system timing cycle, showing the impedance determination, tissue heating and tissue temperature measurement time sub-intervals within an overall system timing cycle. The power control system governs the circuit power on significantly smaller time scales.

As shown in FIG. 8A and FIG. 8B, the overall system timing cycle is typically one second in duration. Over this timing cycle, time markers 810, 812, 816, and 818 bound several time sub-intervals. The sub-interval bounded by time markers 810 and 812 is devoted to determining the electrical impedance of the tissue. This sub-interval is typically 10 milliseconds in duration. Another sub-interval, bounded by time markers 812 and 818, is devoted to the application of RF energy to heat the tissue. This tissue heating sub-interval is typically 900–1000 milliseconds in duration. It is obvious to those skilled in the art that the total time sub-interval for determination of the tissue impedance may be further subdivided into a number of time sub-intervals for sequentially determining the tissue impedance at each of several electrode locations in a multi-channel embodiment.

During each tissue impedance measurement interval, all of the electrodes except the selected electrode are electrically isolated from the system by isolation switches 224 A–B. When isolated, no current flows through the electrode channel. Once all electrodes except that of interest are isolated, a comparatively high RF power 808 (typically 5 Watts) is applied to the single electrode and a tissue impedance determination is made from the current and voltage measurements made with the current and voltage sensors 232. The micro-controller repeats the measurements on each electrode channel in succession until the impedances of the tissue along the current paths from each electrode have been determined.

As described, a comparatively high RF power is applied through the probe electrode on each channel during the time sub-interval for tissue impedance determination. Typically, the power control system holds this first power level constant during the sub-interval by comparing a measured power to a target power level. While powerful currents pass through the tissue, the period of time during which high power is applied is sufficiently brief that no significant tissue heating or other undesirable effects occur. The application of a comparatively high current is necessary during this time interval to ensure a signal to noise ratio that is compatible with an accurate impedance determination. This feature, along with the mitigation of inter-electrode coupling during the measurement time, are major advantages of this invention over prior art methods.

The tissue heating time interval is bounded by time markers 812, 818. Typically, it is 900–1000 ms in duration. During this interval, a much smaller second power level is applied to the tissue 806, typically 0.5 Watt. Control is applied to the circuit to maintain a desired power for each electrode channel throughout. Typically, the power is held constant over this time sub-interval. Although the power for each electrode channel is typically held constant, the system allows for different power levels amongst the electrode channels.

FIG. 8A shows, as an example, the maintenance of a constant power level during the period of tissue heating. The envelope of the RF drive parameter necessary to deliver the constant power 820 is in FIG. 8B. The drive parameter envelope varies during the tissue heating period due to changes in the tissue impedance caused by Joule heating.

FIG. 8A and FIG. 8B also show the time subinterval for tissue temperature measurement. This subinterval is bounded by time markers 816, 818 and occurs near the end of the tissue heating sub-interval. As described, the tissue temperature measurements are made immediately prior to tissue impedance determination in the subsequent system timing cycle. This ensures a close correlation between the measured tissue temperature and impedance.

Figure 9:
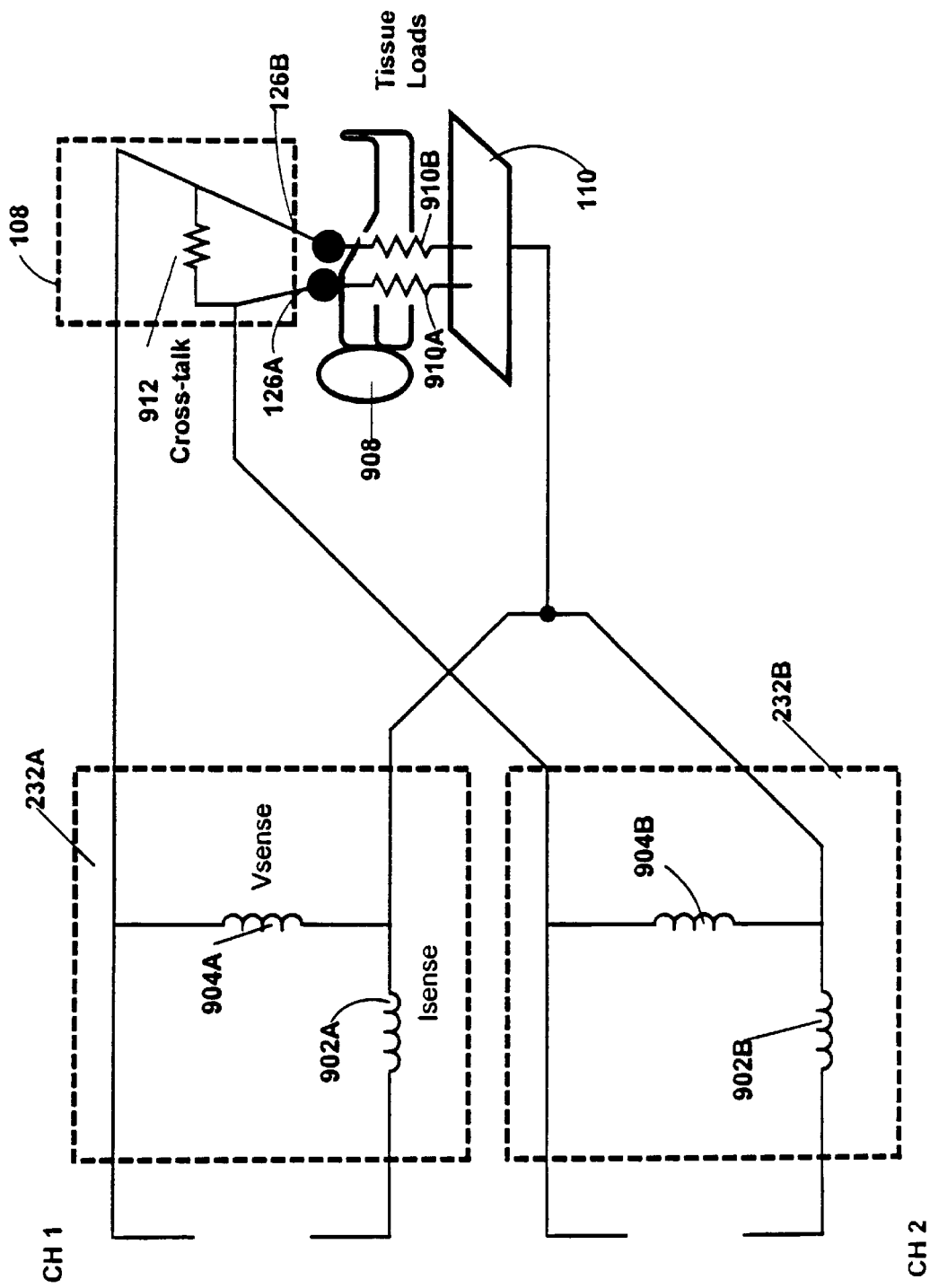
FIG. 9 shows a schematic illustrating electrical hardware elements of the surgical apparatus in a dual-channel embodiment.

FIG. 9 shows a system with two probe electrodes. This two channel system includes current and voltage sensors 232 A–B for each channel, surgical probe 108 electrodes 126 A–B and electrical grounding pad 110. Within each current and voltage sensor 232 A–B, there is a current sensor 902

A–B and voltage sensor 904 A–B. Within the surgical probe 108, there is an electrode 126 A and 126 B for each channel. The electrodes are in contact with tissue 908 and the tissue is in contact with the electrical grounding pad. The equivalent electrical circuit representing the tissue impedance from the electrodes to the grounding pad 910 A–B and the inter-electrode coupling (cross-talk) impedance 912 is also shown.

In FIG. 9, each of the current and voltage sensors 232 A–B are connected to their respective electrodes 126 A–B in the surgical probe 108 as well as to the common electrical grounding pad 110. The tissue is connected to the electrodes and the grounding pad. The grounding pad is connected to the tissue and the current and voltage sensors 232 A–B. When each electrode 126 A–B is connected to the RF generator (not shown), a RF electrical current flows between the tissue and the grounding pad 110. As this occurs, current and voltage sensors 902 A–B, 904 A–B act as a means to determine the RF power applied to the tissue, as well as the electrical impedance of the tissue between the electrode tip and the grounding pad. The relationships between current, voltage, power and impedance are well known to persons skilled in the art. Note that with all of the electrodes except the one of interest isolated by isolation switches 224 A–B (see FIG. 2) there is no significant coupling between the electrodes in the surgical probe causing current flow between them. This is beneficial for an accurate tissue impedance determination. It is obvious to those skilled in the art that the isolating switch may be located elsewhere than shown in FIG. 2.

Figure 10:
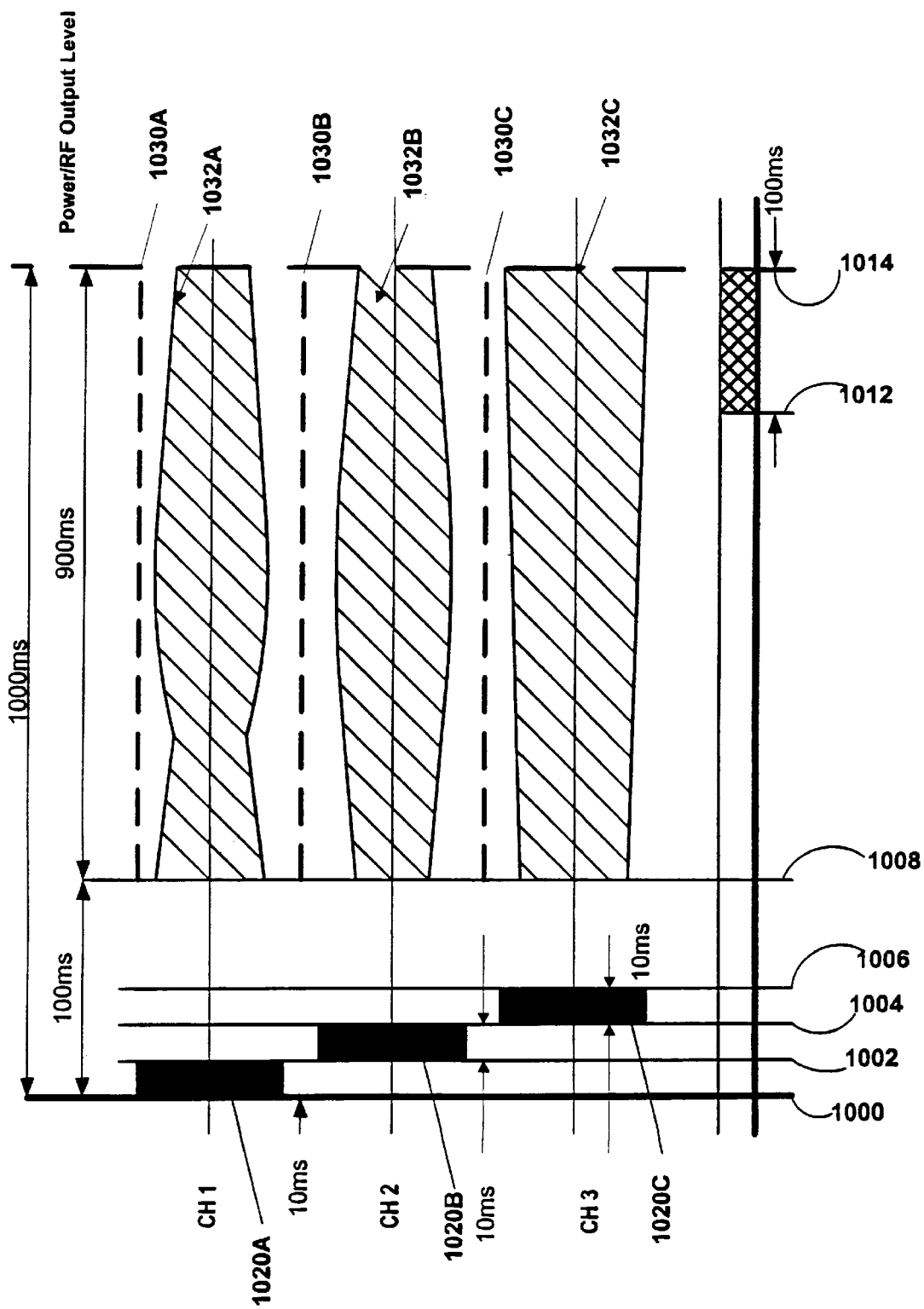
FIG. 10 shows a graph of power versus time and RF power supply drive parameter versus time for a multiple electrode probe illustrating the impedance determination, tissue heating and tissue temperature measurement time subintervals.

FIG. 10 shows a graph of power versus time and RF power supply drive parameter versus time for a multiple electrode probe. FIG. 10 illustrates the impedance determination, tissue heating and tissue temperature measurement time sub-intervals within an overall system timing cycle and is similar to the case of a single channel described in FIG. 8A–B. As in the case of a single channel, the power control systems govern the circuit power on significantly smaller time scales.

As in the case of the single channel, each of the multiple channels has several sub-intervals within the overall system timing cycle of approximately one second duration. The sub-intervals are defined by time markers 1000, 1002, 1004, 1006, 1008, 1012, 1014. For each channel, there is an tissue heating time sub-interval bounded by time markers 1008 and 1014. However, as seen in FIG. 10, the tissue heating time sub-intervals for all channels coincide. Each channel also has an impedance determination sub-interval 1020 A–C that follow each other in sequence. The total impedance determination sub-interval for all channels is bounded by time markers 1000 and 1008 and is typically 100 milliseconds in duration. In this interval time division multiplexing allows each electrode to be electrically isolated from all others while its impedance is measured. The impedance measurement is carried out at a high power level. The high power level allows an accurate determination of impedance. Such a determination would be more difficult at the relatively low power levels used during the tissue heating time sub-interval. Also shown in FIG. 10 is a tissue temperature measurement time sub-interval bounded by time markers 1012, 1014 near the end of the overall timing cycle. The tissue temperature sub-interval is approximately 100 milliseconds in duration. During all of the above time sub-intervals, the power control systems operate on significantly shorter time scales to maintain the desired power 1030 A–C on each channel by varying the RF drive parameters 1032 A–C.

As was the case for a single channel, significantly different power levels are applied to the tissue for the impedance determination and tissue heating. In order to have the signal to noise ratio necessary for an accurate impedance determination a comparatively high power is applied to each electrode channel during that time interval. However, as previously described, the duration of this high power application is sufficiently short so that no significant tissue heating occurs. During the subsequent tissue heating interval, a much lower RF power is applied to the tissue on all channels. While the power level during this interval is comparatively low, the application persists over a time interval several orders of magnitude longer than that for the tissue impedance determination. During the period of tissue heating, the power circuits of each channel are controlled to maintain a constant power under a varying impedance. A tissue temperature measurement is made near the end of the heating interval.

Figure 11:
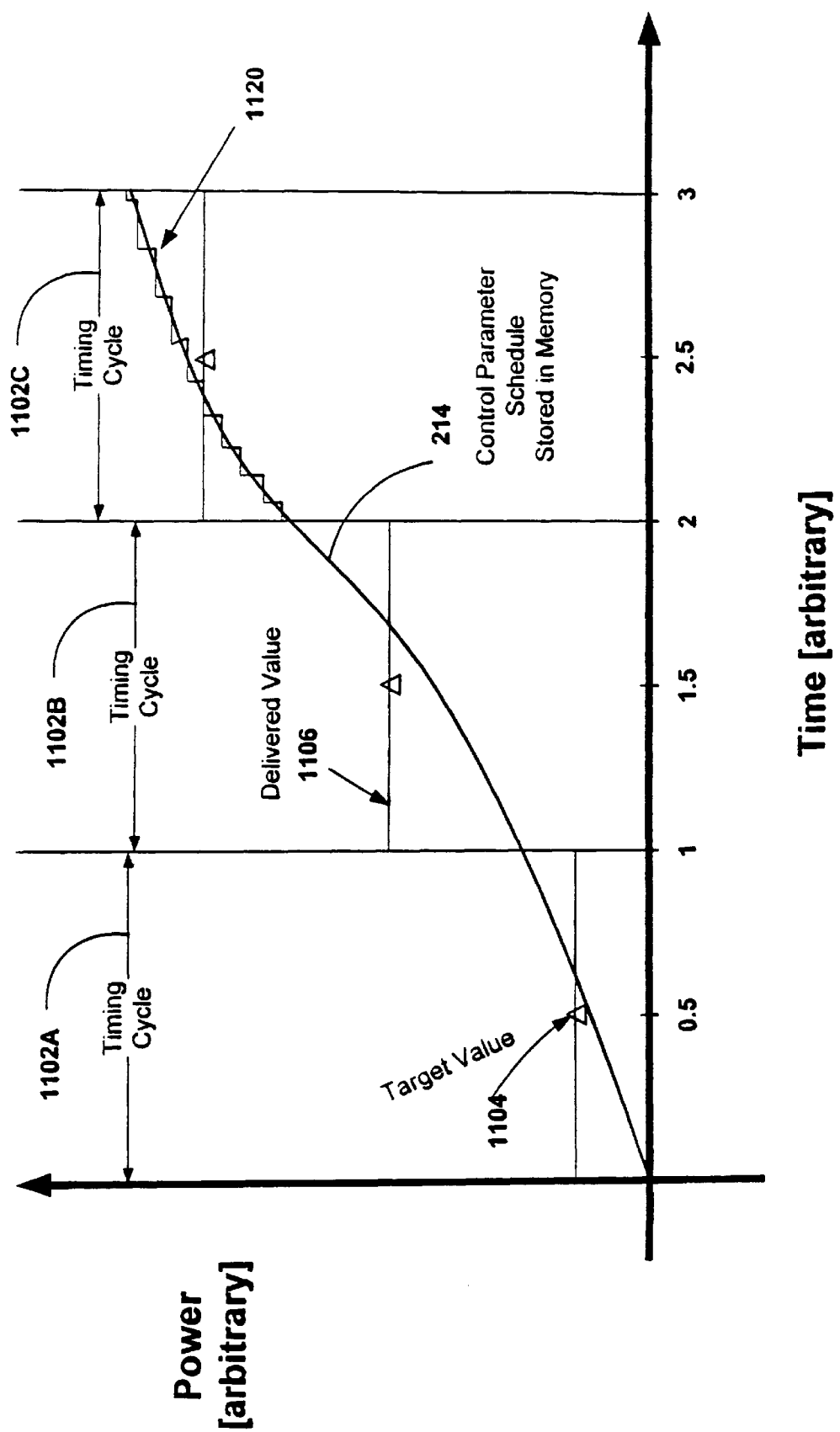
FIG. 11 shows a graph of power versus treatment time illustrating a control parameter time schedule, target value and value delivered by the control system.

FIG. 11 shows a graph of power versus treatment time illustrating a power time schedule, target power and power delivered by the power control system under a exemplary control law. It illustrates the use of the power control system to accomplish the intended medical function by delivering prescribed power to the tissue site. FIG. 11 shows a control parameter schedule 214, with power as the control parameter. Three overall system timing cycles 1102 A–C of one second duration each are shown. During each overall system timing cycle, the micro-controller 202 (see FIG. 2) receives inputs from power and temperature measurements and executes control laws based on those and other system parameters. Under an exemplary control law, the micro-controller calculates a target value of power 1104 and control is applied to each electrode channel 204 A–B (see FIG. 2) to maintain a constant delivered value 1106 of power over the timing interval. The target value of the control parameter may be updated as desired to follow the control parameter schedule to a desired accuracy. This is illustrated by the comparative frequency of target value updates 1120 in timing cycles 1102 C. It is obvious to those skilled in the art that the system can be configured to follow other appropriate control parameters, such as tissue temperature. It is equally obvious to those skilled in the art that the system can be configured to follow other power control laws.

Figure 12:
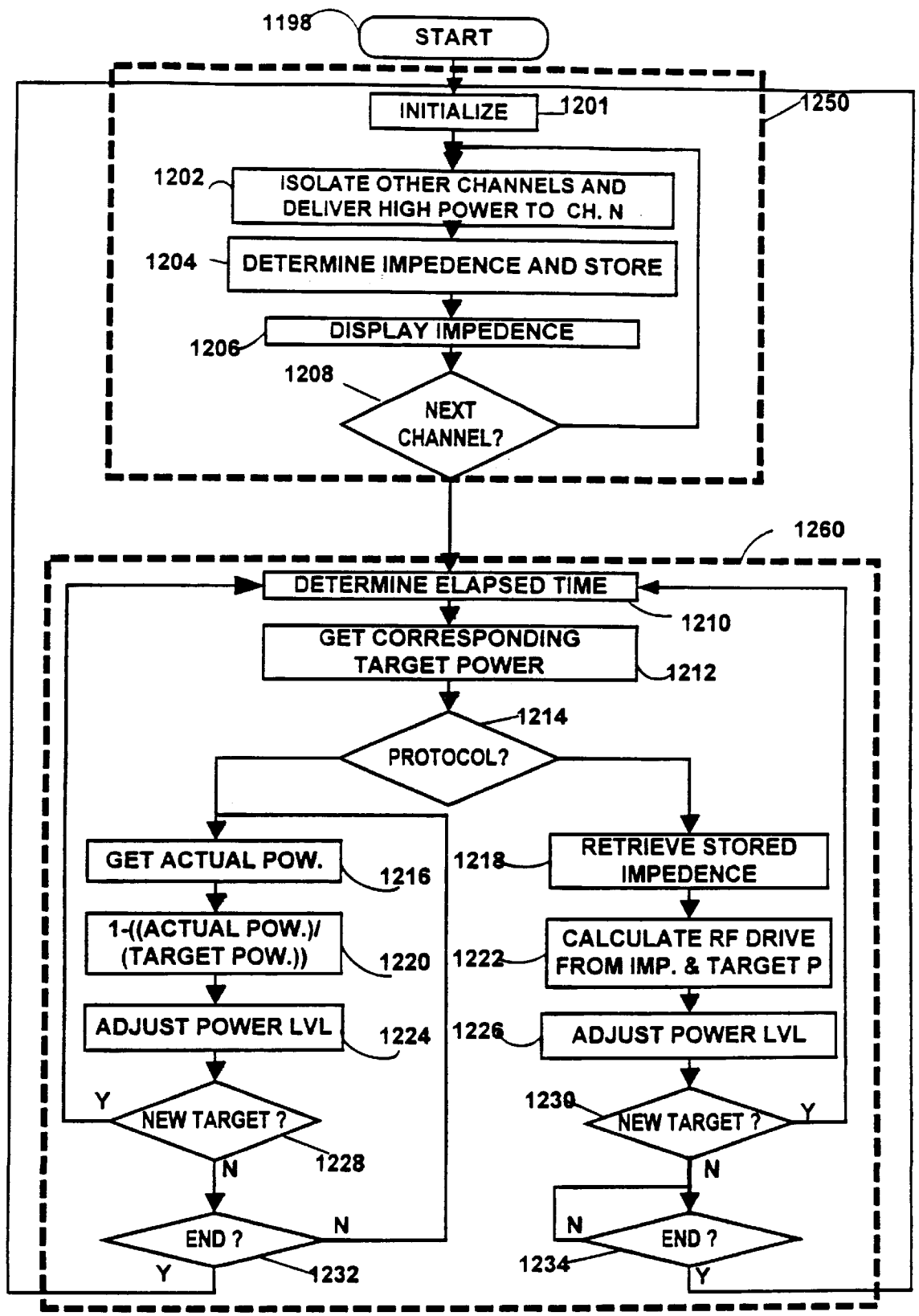
FIG. 12 shows a process flow chart illustrating the method for tissue impedance determination and power control.

FIG. 12 shows a process flow chart for this method of tissue electrical impedance determination and electrical power control. The process shown in FIG. 12 is implemented by micro-controller 202 (see FIG. 2). The process begins by startup and initialization of the device in process block 1198. During startup, the system initializes itself, performs several self-tests and uploads information from the memory and receives information input by the user from the front panel. Clocks and other variables requiring initialization are set in block 1201.

Within the overall system timing cycle illustrated, control first passes to sequence 1250 where the tissue impedance determinations are accomplished. In 1202, the micro-controller 202 electrically isolates all but the first channel and then applies a comparatively high RF power only to that channel. Control then passes to process block 1204 where the electrical impedance in the tissue is determined from measurements of current and voltage in the energized channel. The resulting the value is stored. Control then passes to process block 1206 where the value of the tissue impedance is displayed to the user at the user input and display panel 102 (see FIG. 1). Control then passes to decision block 1208 where the system can repeat the preceding process for subsequent electrode channels or proceed once the tissue impedance across all of the electrodes is determined.

Once the tissue impedance has been measured at each electrode channel, control passes to sequence 1260 were the tissue heating is accomplished. Sequence 1260 begins with block 1210 where the micro-controller 202 (see FIG. 2) determines the elapsed time from the start of the treatment. This corresponds to the abscissa shown in FIG. 11. Following this, control passes to process block 1212 where the micro-controller calculates a target value of the control parameter. In this exemplary embodiment, power is the control parameter. Thus, the micro-controller calculates a target power from the control parameter schedule 214 (see FIG. 2). Control then passes to decision block 1214.

At decision block 1214, the system chooses a power control protocol. In one embodiment, with power as the control parameter, there are two power control protocols to choose from. Under the first power control protocol, the power delivered to the tissue site from an electrode is calculated from the measurements of current and voltage in process block 1216. Control then passes to process block 1220, where the fractional difference between the actual power delivered and the target power, or fractional error, is calculated. Control then passes to process block 1224 where a RF drive parameter is adjusted, altering the RF power to minimize the fractional error and maintain the constant target power delivered through the electrode. This value is communicated to the power control system 220 (see FIG. 2). Control then passes to decision block 1228 where an evaluation is made as to whether an update of the targeted value of power is desired. If a new target value for the power is not desired, control passes to decision block 1232. At decision block 1232, an evaluation is made as to whether the tissue heating time limit is over. If it is, then the system returns to sequence 1250 and another overall system timing cycle begins with tissue impedance measurements on each electrode channel.

An alternate power control protocol proceeds from decision block 1214 by retrieving the stored tissue impedance at process block 1218. Control then passes to process block 1222 where the RF drive parameter required to deliver the target value of power is calculated directly, assuming the stored tissue impedance value from the previous impedance determination interval. Control then passes to process block 1226 where the RF drive parameter is adjusted to achieve the target value. This value is communicated to the power control system 220 (see FIG. 2). Control then passes to decision block 1230 where an evaluation is made as to whether an update of the targeted value of power is desired. If a new target value for the power is not desired, control passes to decision block 1234. At decision block 1234, an evaluation is made as to whether the tissue heating time period is over. If it is, then the system returns to sequence 1250 and another overall system timing cycle begins with tissue impedance measurements on each electrode channel.

In an alternate embodiment of the invention temperature rather than power constitutes the control parameter in the control parameter schedule 214. In that embodiment the protocol followed compares current, previous temperature, and target temperature and impedances of each electrode and determines the amount of error in the desired versus actual temperature of the surgical site. Using this determination power is adjusted accordingly and the appropriate "heating" voltages i for maintaining the target temperature at the surgical site are imposed by the waveform generator 222 A–B and the power drive 226 A–B.

Figure 13B:
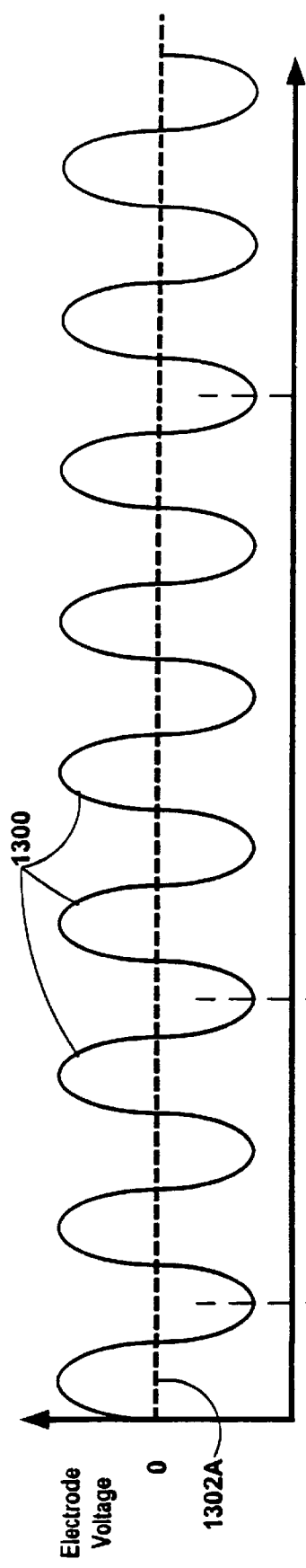
FIG. 13B shows electrode voltage versus time for an electrode at a reference impedance.
Figure 13A:
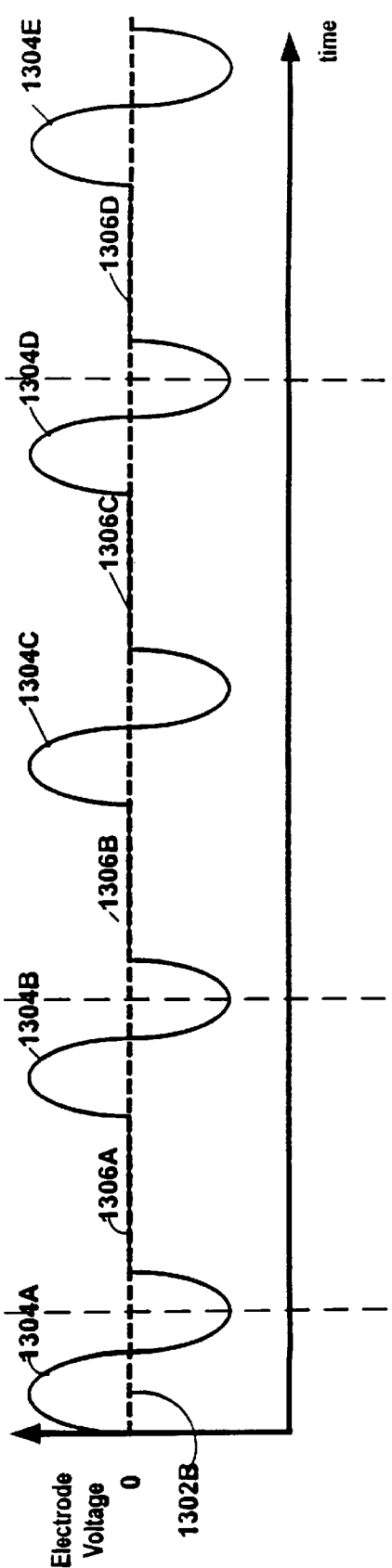
FIG. 13A shows electrode voltage versus time for an electrode at a lower than reference impedance, illustrating the use of null cycles for controlling multi-pole operation.

FIG. 13A and FIG. 13B show the electrode voltage (monopolar mode) versus time for two electrodes illustrating the novel use of null intervals to control power delivery and multi-pole operation. The electrode of FIG. 13B delivers power across tissue with a given reference electrical impedance. The electrode of FIG. 13A delivers power across tissue with a comparatively smaller impedance. RF voltage wavetrain 1300, and voltage wavelets 1304 A–E oscillate about null crossing 1302 A–B. By removing wave cycles by means of isolation switches 224 A–B (see FIG. 2) at the lower impedance electrode, the electric power delivered to the tissues (equal to the electrode voltage squared divided by the impedance) at both sites can be matched over tissue heating time scales.

In the preferred embodiment, only full waves are nulled. Arbitrary nulling results in both high and low frequency Fourier signal components that affect the other medical electronics and the patient, respectively. Half-wave nulling could cause the patient to accumulate charge due to the current-voltage lag caused by tissue capacitance and inductance.

In an alternate embodiment, a constant voltage source is used. This can simplify the power and impedance measurements.

During a null period, an inter-electrode current driven by their potential difference (bipolar mode) is prevented in the preferred embodiment by connecting the nulled electrode to an extremely high impedance. If a strictly monopolar delivery is desired after the null period, the RF cycles are resumed in phase with those of the other electrode thereby avoiding any bipolar effects. In an alternate embodiment, the RF cycles may be resumed out of phase and the resulting electrode potential difference will drive an interelectrode current.

FIG. 14 illustrates the monopolar, multipolar and combined monopolar/multipolar modes of operation. Two probe electrodes 126 A–B are shown. In monopolar operation, current 1450 flows due differences in electric potential between the electrodes 126 A–B and the floating ground provided by the grounding pad (not shown). There is no inter-electrode current. It is obvious to persons skilled in the art that elements other than the grounding pad can be substituted equivalently, for example an electrode connected to a floating ground. In the bipolar mode of operation, the ground pad is removed from the circuit either physically or effectively by connecting it to an extremely large impedance. In bipolar operation, current 1460 flows between the probe electrodes 126 A–B due to the differences in electric potential. There is no current flow to the ground pad. Multipolar operation is an extension of bipolar operation with more than two probe electrodes. Combined monopolar and bipolar operation occurs when potential differences drive currents both to the floating ground 1480 and between the electrodes 1470. Note that the extent of the treatment zone is affected by the mode of operation.

A significant advantage of the present invention is the availability of a combined monopolar and bipolar mode of operation in addition to a purely monopolar mode. In the monopolar mode, the same RF voltage signal is applied to each probe electrode 126 A–B (see FIG. 1B) and current flows from the electrodes to an indifferent ground pad electrode placed in contact with the patient. Since the control system maintains the two probe electrodes 126 A–B at the same potential, no current flows between them. Current only flows between each electrode and the electrical ground pad. However, by changing the amplitude, frequency or phase of one of the RF signals, a potential difference is created across the probe electrodes 126 A–B and current flows between them. This provides combined monopolar and bipolar operation. Combined monopolar and bipolar operation allows a larger tissue volume to be heated as shown in FIG. 14.

Figure 15A:
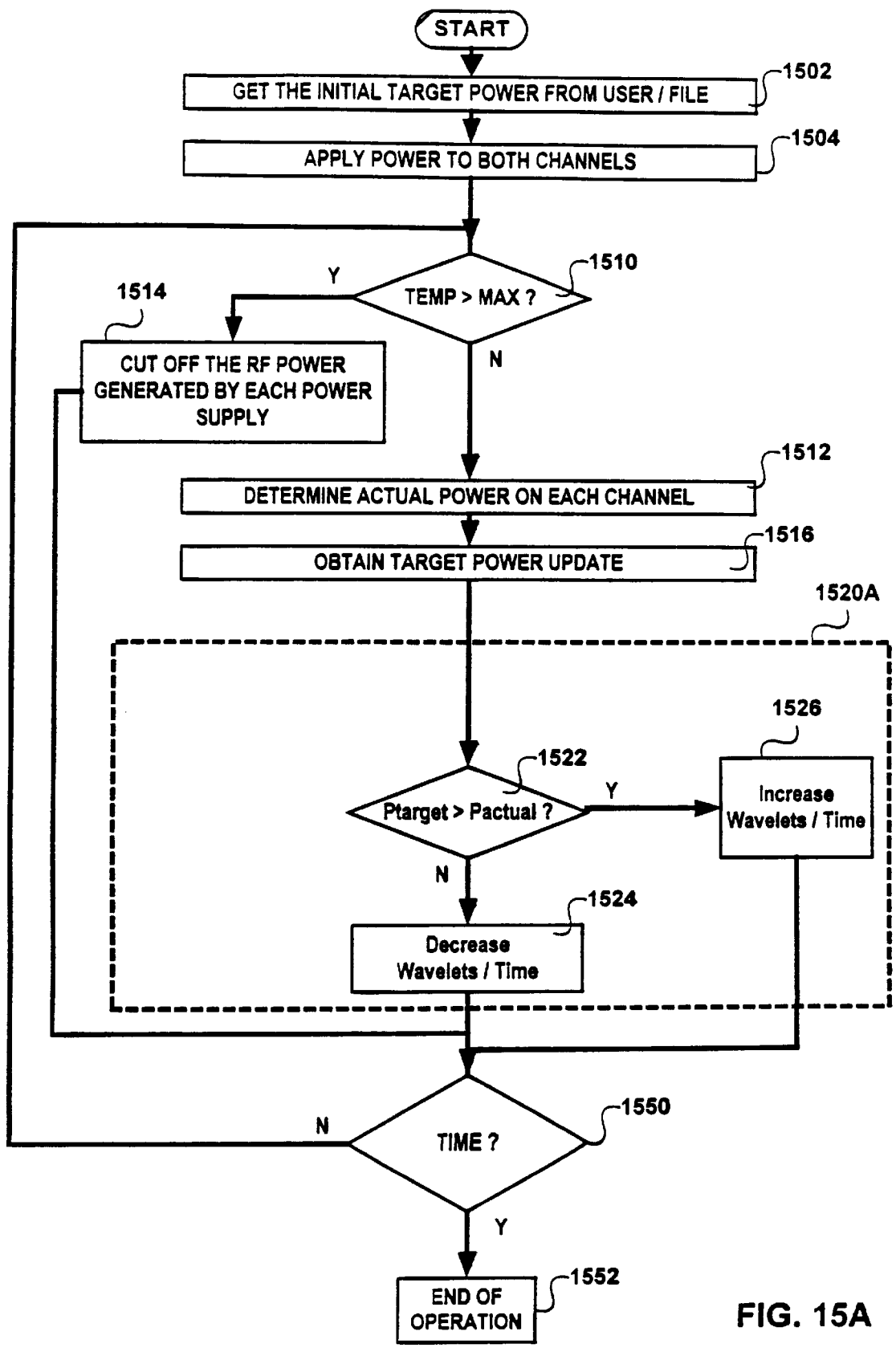
FIGS. 15A–B show process flow diagrams for alternate embodiments of the method for multi-electrode power delivery of the present invention.
Figure 15B:
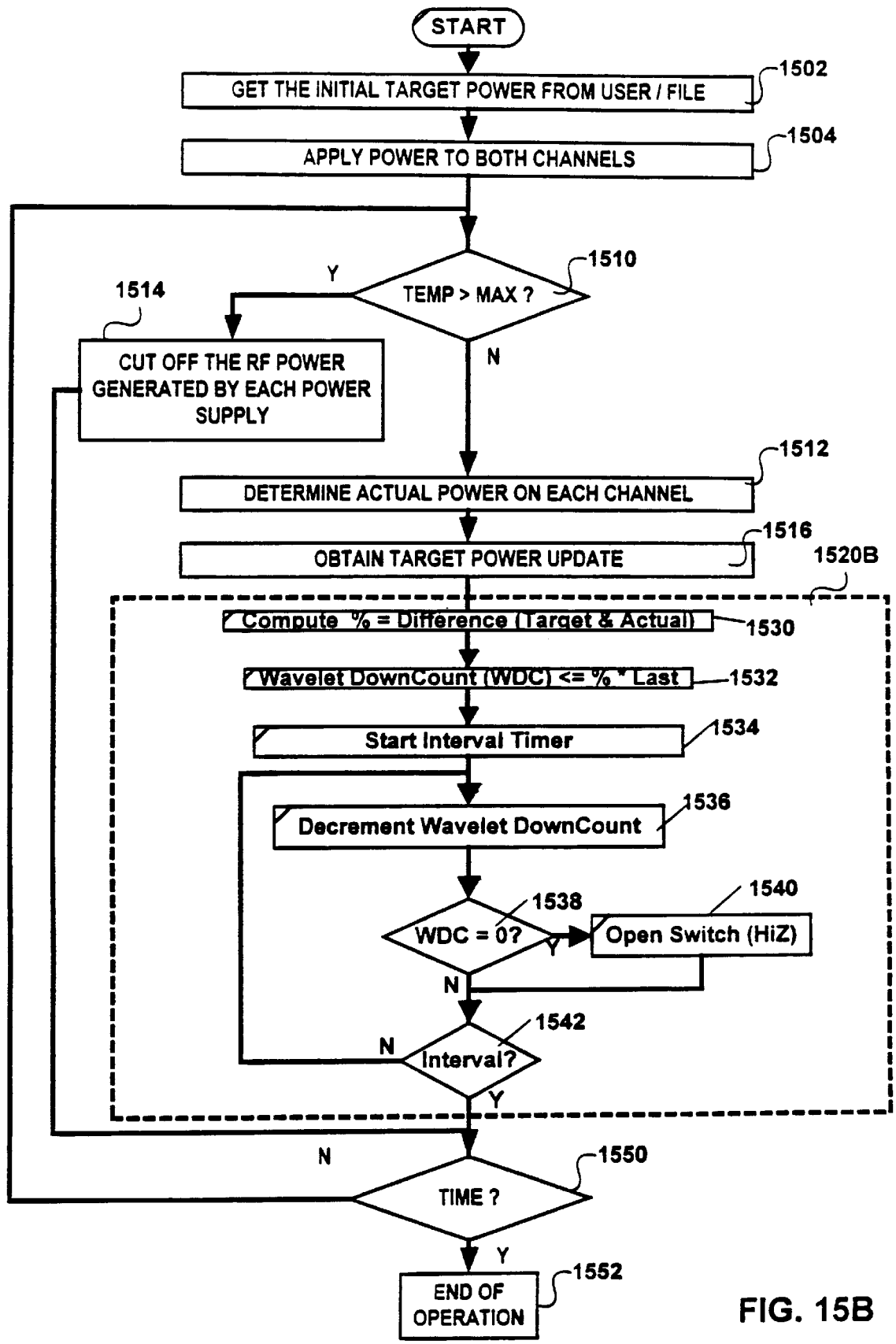

FIG. 15A and FIG. 15B show flowcharts for the RF wave cycles adjustment process for a two electrode embodiment. The processes shown in FIGS. 15A–B is implemented by the micro-controller 202 (see FIG. 2). In FIG. 15A, the process begins in block 1502 where an initial value for the target power is obtained from either the user input and display panel 102 or memory unit 210. Control then passes to block 1504 where electric power is applied to the tissue through the electrodes. Control then passes to decision block 1510 where a determination is made whether the tissue temperature exceeds a predetermined maximum. If the maximum tissue temperature is exceeded, RF power is cut off in process block 1514. If the tissue temperature is not exceeded, control passes to process block 1512 where the power delivered to the tissue is determined by power measurement system 234 A–B (see FIG. 2). Control then passes to process block 1516 where an updated target value for the power corresponding to the surgical time is obtained from memory unit 210. Control then passes to control sequence 1520 A where the null periods are determined, thereby altering the applied power. In the preferred embodiment, the null intervals are applied at every other wave cycle when nulling is required. The thermal lag of the tissue response integrates the effect of this quantized (fall on-half nulled-full off) range.

In control sequence 1520, a determination is made at decision block 1522 whether the target value for the power exceeds the power actually delivered to the surgical site, as determined by the power measurement system 234 A–B (see FIG. 2). In the case that the actual power delivered to the surgical site is less than the target value, null periods are removed to increase the applied power. In the case that the actual power delivered to the surgical site is greater than the target value, null intervals are added to decrease the applied power in process block 1524. If necessary, null intervals are removed in process block 1526. Control then passes to decision block 1550 where a determination is made whether the surgical time is expired. If the surgery continues, control passes to decision block 1510 where the measured tissue temperature is again compared to a predetermined value. If the surgery is finished, process block 1552 stops the operation.

FIG. 15B shows detail of control sequence 1520 B where the null intervals are implemented. The process flow is as described in FIG. 15A up to block 1516. In process block 1530 micro-controller 202 (see FIG. 2) computes the difference between the target value of power and that actually delivered relative to the actually delivered power. Control then passes to process block 1532 where the relative error calculated in block 1530 is used to correct the number of voltage wavelets 1304 A–E (see FIG. 13A) per unit time that are passed to the tissue. This integer value is stored in a wavelet down counter in micro-controller 202 (see FIG. 2). Control then passes to block 1534 that begins a control time interval over which RF wavelets are counted. The preferred interval is an integer multiple of the inverse RF frequency and is approximately one second in duration. Control then passes to block 1536 where the wavelet down counter decrements after each time period corresponding to the inverse RF frequency. Control then passes to decision block 1538 where a determination is made whether the down counter has reached zero, indicating a null interval is to commence. If a null interval 1306 A–D (see FIG. 13A) is to commence, the electrode to be nulled has voltage removed and is switched to a extremely large impedance circuit element to prevent any current flow in process block 1540. If the down counter indicates by a nonzero value that a null interval is not desired, the electrode remains active in an active interval. Control then passes to decision block 1542 where a determination is made whether the control time interval is finished. Control then passes to decision block 1550 where a determination is made whether the surgical time is expired. If the surgery continues, control passes to decision block 1510 where the measured tissue temperature is again compared to a predetermined value. If the surgery is finished, process block 1552 stops the operation.

Figure 16:
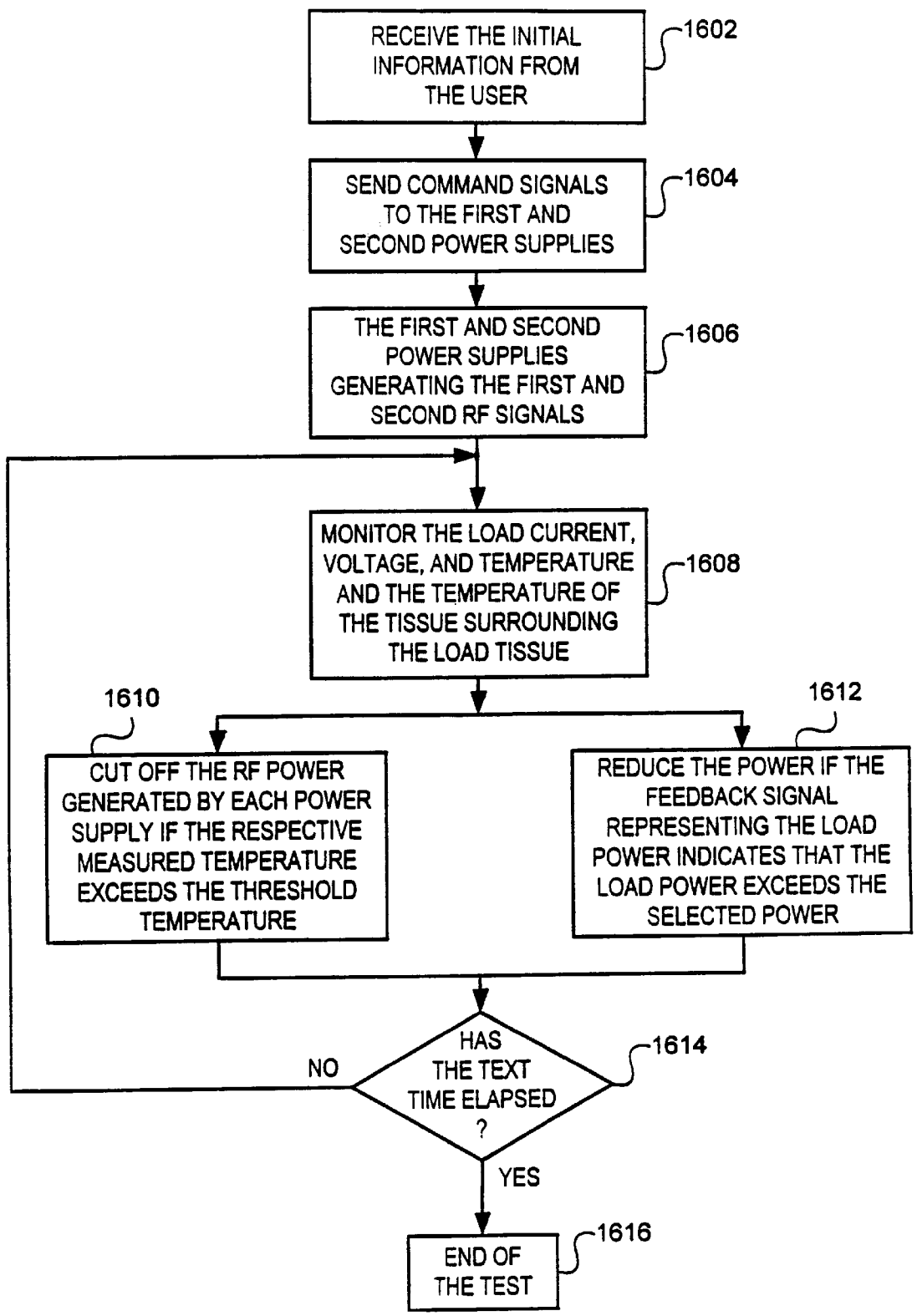

FIG. 16 is a flow chart of the sequence of operations of the RF ON mode of the RF power delivery system of the present invention. The user inputs the initial information in step 1602. Initial information includes frequency, phase, power, and time duration for each RF signal. This information is typically entered using the keypad provided on the front panel. In step 1604, the initial information is received by microcontroller 202, which generates digital command signals that are sent to control systems 220 A–B.

In step 1606, the two power delivery channels generate two independent RF signals, with each RF signal having a selected power level, frequency, and phase. The RF power level is increased gradually toward the desired power level, at which time the RF signals are applied to their respective electrodes.

To protect the patient from receiving an excessive amount of RF energy, the RF power delivered to the target tissue is monitored by two different methods. The RF power levels are monitored either directly or through their effects on the target and surrounding tissues as indicated by the various temperature measurements. The RF power is monitored directly in step 1608. Sensors measure the RF currents and RF voltages at the electrodes on the probe 108 of the surgical instrument 106. The power delivered to the target tissue is then calculated by the power measurement systems 234 A–B, as previously discussed.

Steps 1610 and 1612 may be performed simultaneously. In step 1612, the power levels calculated by power measurement systems 234 A–B are compared with their respective selected power levels. The generated power levels are reduced if the measured power levels exceed their respective selected power levels. In step 1610, RF power is terminated if the measured temperature of the target or the surrounding tissue exceeds a threshold temperature. RF power is delivered to the target tissue for a time duration as selected by the user. In step 1604, after the selected time duration has expired, the power system enters the RF OFF mode.

The dual-channel RF power delivery system of the present invention provides numerous advantages over prior art power delivery systems. The power delivery system performs a battery of self-tests, including a test of each waveform generator 222 A–B by loading the generator with an internal test load. Precision reference voltage sources (not shown) are provided which can be used for calibrating the thermocouples. This test is implemented through a multiplexing scheme in which each thermocouple is individually calibrated using the reference voltages.

The use of multiplexers also allows temperature information to be easily obtained across the patient isolation barrier. An isolation barrier, such as a transformer-coupled or optically-coupled isolation amplifier, is usually required between a patient and a microcomputer. The use of the multiplexer arrangement avoids the need for separate isolation amplifiers for each thermocouple.

Another significant advantage of the power delivery system of the present invention is the availability of a combined monopolar and bipolar mode. In the monopolar mode, the same RF signal is applied to each electrode and current flows from the electrodes to an indifferent electrode placed on the patient's back. The two RF signals are at the same power level, frequency, and phase. Therefore, the two electrodes are at the same voltage levels and no current flows between them. Current only flows between each electrode and the indifferent electrode on the patient's back. However, by changing the power level, frequency or phase of one of the RF signals, a voltage is created across the electrodes 26 and current flows between them. This provides bipolar ablation in combination with monopolar ablation. Differential sensor measures the difference in the current flows from the two electrodes to the indifferent electrode. Bipolar ablation in combination with monopolar ablation allows a larger tissue volume to be ablated without increasing the RF energy applied to the patient.

The results of laboratory tests in which one of the RF signals was varied in phase, frequency, and phase and frequency are shown in Table 1. Turkey breasts were used as the target tissue.

the READY switch on the front panel 104 is pressed, the system enters the READY mode.

In the READY mode, low-level RF signals are generated intermittently to allow impedance measurements to be made. The UP/DOWN POWER switch allows the desired power level for each electrode 26 to be incremented or decremented by 0.1 watt. The power range is limited to 0–15 watts. The UP/DOWN TIMER switch allows the desired time duration for each electrode to be incremented or decremented by 1 second. The maximum time duration is typically limited to 10 minutes.

In the READY mode, temperature measurements are taken from each thermocouple. The two stylet temperatures are read ten times per second and a filtered average is displayed on the front panel, which is updated once per second. The urethral and rectal temperatures are also read ten times per second and a filtered average of the urethral temperature and a filtered maximum rectal temperature are displayed on the front panel 104. Impedance of the target tissue at the two electrodes is measured by intermittently applying a low powered RF signal to each electrode and

TABLE 1

| | | TOTAL POWER (WATTS) | THE POWER OF THE FIRST ELECTRODE | THE POWER OF THE SECOND ELECTRODE | TIME (MIN.) | LESION VOLUME |
|---|---|---|---|---|---|---|
| 1. | ONE SUPPLY | 8.2 | 4.1 | 4.1 | 5 | 1653 |
| 2. | TWO POWER SUPPLIES AND PHASE DIFFERENCE | 4.1 (each supply) | 4.1 | 4.1 | 5 | 3600 |
| 3. | TWO POWER SUPPLIES AND FREQUENCY DIFFERENCE | 4.1 (each supply) | 4.1 | 4.1 | 5 | 2135 |
| 4. | TWO POWER SUPPLIES AND PHASE AND FREQUENCY DIFFERENCE | 4.1 (each supply) | 4.1 | 4.1 | 5 | 4582 |

In the first case, the same RF signal of 4.1 watts was applied to each electrode 26 for a total RF power level of 8.2 watts. In the second, third, and fourth cases, each RF signal had a power level of 4.1 watts, but the frequency, phase, and frequency and phase of one of the RF signals were varied. In the second case, the two RF signals were out of phase. In the third case, one RF signal had a frequency of 460 KHz and the other RF signal had a frequency of 480 KHz. In the fourth case, one RF signal had a frequency of 460 KHz the other RF signal had a frequency of 480 KHz and the RF signals were out of phase. In all four cases, the power was delivered to the target tissues for 5 minutes. In the fourth case, with the two RF signals out of phase and at different frequencies, the lesion volume was about three times the volume in the first case, which used identical RF signals.

The dual-channel RF power delivery system has five different modes of operation, including SELF-TEST, STAND-BY, READY, RF ON, and RF OFF. When the power system is first turned on, the system enters the SELF-TEST mode. Various self-tests are performed in this mode, including a microprocessor test, RAM read/write test, a ROM test, an RF power generation and measurement test, and a temperature measurement system test. When the various tests are successfully passed, the system enters the STAND-BY mode. If the test is not passed, an error message appears on the display.

In the STAND-BY mode, power is supplied for the various functions, but none of the functions is active. When measuring the resulting RF voltage and RF current. The microcontroller 202 calculates the impedance by dividing the RF voltage by the RF current.

In the RF ON mode, RF power is generated and the measurement, control, display and timer functions are active. The RF ON mode is activated either by depressing the foot switch or the RF ON/OFF switch. Depressing the STANDBY switch or the foot switch reactivates the STANDBY mode. The RF OFF mode is automatically activated when the selected time durations for both stylets have been reached, or if any of the measured temperatures exceed predefined limits.

From the foregoing, it will be appreciated that the present invention represents a significant advance in the field of RF ablation devices. Although several preferred embodiments of the invention have been shown and described, it will be apparent that other adaptations and modifications can be made without departing from the spirit and scope of invention. Accordingly, the invention is not to be limited, except as by the following claims.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art.

What is claimed is:

1. A method for controlling power delivery in an electrosurgical instrument including a plurality of channels for delivery of an energy to a surgical site, and the method for controlling power comprising the acts of:

measuring in a first time interval, the impedance of each of said channels, and each channel sequentially isolated from others of the channels to determine impedance;

generating in a second time interval for each of the channels a signal proportional to an actual power in each of the channels, and the signal proportional to the actual power derived from a product of low frequency signals proportional to current and voltage of each of the channels and the low frequency signals derived from high frequency signals corresponding to a current and a voltage on each of the channels; and adjusting in the second time interval, power levels of the channels to minimize a difference between a measured value of a control parameter and a target value of the control parameter, to deliver the energy to the surgical site.

2. The method of claim 1, further comprising the acts of:

computing differences between a target power and an actual power delivered to the at least one electrode to establish an amount by which to increase and to decrease the power in the first oscillating signal; and modulating a driver signal generated by the driver to increase and to decrease an integer number of whole wavelengths of the driver signal to produce the first oscillating signal, responsive to said computing act.

3. The method of claim 1, wherein the measuring act further comprises the acts of:

measuring a first power level in a first of the plurality of channels during a first measurement interval in which the first of the plurality of channels is electrically isolated from the second of the plurality of channels; and measuring a second power level in the second of the plurality of channels during a second measurement interval in which the second of the plurality of channels is electrically isolated from the first of the plurality of channels.

4. The method of claim 1, wherein the generating act farther comprises the acts of:

generating a first signal and a second signal proportional respectively to a sum and a difference of a current and a voltage delivered by the first of the plurality of channels to the surgical site;

forming a third and a fourth signal proportional respectively to peak voltage levels in the first and the second signals;

producing a fifth signal and a sixth signal proportional respectively to a difference and a sum of the third signal and the fourth signal;

multiplying the fifth and the sixth signals to produce a power signal equivalent to an actual power delivered by the first of the plurality of channels to the surgical site.

5. A method for controlling power delivery in an electrosurgical instrument including a plurality of channels for delivery of an energy to a surgical site, and the method for controlling power comprising the acts of:

measuring in a first time interval, the impedance of each of plurality of channels by sequentially isolating each of the plurality of channels from others of the plurality of channels; and computing in a second time interval differences between a target power and an actual power delivered to the plurality of channels to establish an amount by which to increase and to decrease the power in the plurality of channels; and modulating in the second time interval a driver signal for each of the plurality of channels to increase and to decrease an integer number of whole wavelengths of the driver signal to produce power levels on each of the plurality of channels, responsive to the computing act.

6. The method of claim 5 further comprising the act of:

generating for each of the plurality of channels a signal proportional to an actual power in each of the plurality of channels, and the signal proportional to the actual power derived from a product of low frequency signals proportional to a current and a voltage on each of the plurality of channels and the low frequency signals derived from high frequency signals corresponding to the current and the voltage on each of the plurality of channels.

7. The method of claim 5, wherein said act of measuring further comprises the acts of:

measuring a first power level of a first of the plurality of channels during a first measurement interval in which the first of the plurality of channels is electrically isolated from a second of the plurality of channels; and measuring a second power level of the second of the plurality of channels during a second measurement interval in which the second of the plurality of channels is electrically isolated from the first of the plurality of channels.

8. The method of claim 5 further comprising the acts of:

computing differences between a target power and an actual power delivered to the at least one electrode to establish an amount by which to increase and to decrease the power in the first oscillating signal; and modulating a driver signal generated by the driver to increase and to decrease an integer number of whole wavelengths of the driver signal to produce the first oscillating signal, responsive to said computing act.

9. A method for controlling power delivery in an electrosurgical instrument including a plurality of channels for delivery of an energy to a surgical site, and the method for controlling power comprising the acts of:

generating for a first of the plurality of channels a signal proportional to an actual power, and the signal proportional to the actual power derived from a product of low frequency signals proportional to current and voltage of the first of the plurality of channels and the low frequency signals derived from high frequency oscillating signals corresponding to a current and a voltage of a first oscillating signal of the first of the plurality of channels;

computing differences between a target power and an actual power delivered to the first of the plurality of channels to establish an amount by which to increase and to decrease the power in the first oscillating signal; and modulating a driver signal generated by the driver to increase and to decrease an integer number of whole wavelengths of the driver signal to produce the first oscillating signal, responsive to said computing act.

10. The method of claim 9 further comprising the acts of:

determining a target value for a control parameter for the first channel and the second channel;

measuring a first power level of the first channel during a first measurement interval in which the first channel is electrically isolated from the second channel;

measuring a second power level of the second channel during a second measurement interval in which the second channel is electrically isolated from the first channel; and adjusting the first power level and the second power level to minimize a difference between a measured value of the control parameter and the target value of the control parameter, to deliver the energy to the surgical site during a heating interval.

11. The method of claim 9, wherein the act of generating further comprises the acts of:

generating a first signal and a second signal proportional respectively to a sum and a difference of a current and a voltage delivered by the first of the plurality of channels to the surgical site;

forming a third and a fourth signal proportional respectively to peak voltage levels in the first and the second signals;

producing a fifth signal and a sixth signal proportional respectively to a difference and a sum of the third signal and the fourth signal;

multiplying the fifth and the sixth signals to produce a power signal equivalent to an actual power delivered by the first of the plurality of channels to the surgical site.

12. The method of claim 9, wherein the act of modulating further comprises the acts of:

computing differences between a target power and an actual power delivered to the at least one electrode to establish an amount by which to increase and to decrease the power in the first oscillating signal; and modulating a driver signal generated by the driver to increase and to decrease an integer number of whole wavelengths of the driver signal to produce the first oscillating signal, responsive to said computing act.

13. An apparatus for power measurement in an electro-surgical instrument including a first channel for delivery of energy to a surgical site, and the apparatus for power measurement comprising:

sensors for producing a voltage signal and a current signal proportional to a voltage and a current delivered by the first channel to the surgical site;

a first summer and differencer for respectively, summing the voltage signal together with the current signal to produce a first signal and for differencing the voltage signal with the current signal to produce a second signal;

a peak detector coupled to the first summer and differencer for forming a third and a fourth signal proportional respectively to peak voltage levels in the first and the second signals;

a second summer and differencer for producing a fifth signal and a sixth signal proportional respectively to a difference and a sum of the third signal and the fourth signal; and a multiplier for multiplying the fifth and the sixth signals to produce a power signal equivalent to an actual power delivered by the first channel to the surgical site.

14. An apparatus for controlling electrical cross-talk in an electro-surgical instrument including a driver, a first electrode and a second electrode and a ground for delivery of power to a surgical site, and the apparatus for controlling cross-talk comprising:

a power measurement circuit for computing differences between a target power and an actual power delivered to the first electrode and the second electrode to establish an amount by which to increase and to decrease the power emanating from the first electrode and the second electrode the power measurement circuit including a microcontroller; and a waveform generator coupled to the microcontroller, the microcontroller modulating a driver signal generated by the driver to increase and to decrease an integer number of whole wavelengths of the driver signal to produce a first oscillating signal measured at the first electrode and a second oscillating signal measured at the second electrode.

* * * * *